US011505805B2

(12) United States Patent
Zhang et al.

(10) Patent No.: US 11,505,805 B2
(45) Date of Patent: Nov. 22, 2022

(54) POLYNUCLEOTIDE AND METHOD FOR CONTROLLING INSECT INVASION

(71) Applicant: BEIJING DABEINONG BIOTECHNOLOGY CO., LTD., Beijing (CN)

(72) Inventors: Aihong Zhang, Beijing (CN); Derong Ding, Beijing (CN); Qing Tao, Beijing (CN); Xiaojiao Li, Beijing (CN)

(73) Assignee: BEIJING DABEINONG BIOTECHNOLOGY CO., LTD., Beijing (CN)

( * ) Notice: Subject to any disclaimer, the term of this patent is extended or adjusted under 35 U.S.C. 154(b) by 0 days.

(21) Appl. No.: 15/733,802

(22) PCT Filed: May 7, 2019

(86) PCT No.: PCT/CN2019/085800
§ 371 (c)(1),
(2) Date: Nov. 30, 2020

(87) PCT Pub. No.: WO2019/228151
PCT Pub. Date: Dec. 5, 2019

(65) Prior Publication Data

US 2021/0214744 A1 Jul. 15, 2021

(30) Foreign Application Priority Data

May 31, 2018 (CN) ......................... 201810550207.4

(51) Int. Cl.
| | |
|---|---|
| *C12N 15/82* | (2006.01) |
| *A01N 63/60* | (2020.01) |
| *A01N 25/02* | (2006.01) |
| *C12N 15/113* | (2010.01) |

(52) U.S. Cl.
CPC ......... *C12N 15/8286* (2013.01); *A01N 25/02* (2013.01); *A01N 63/60* (2020.01); *C12N 15/113* (2013.01); *C12N 15/8218* (2013.01); *C12N 2310/14* (2013.01)

(58) Field of Classification Search
None
See application file for complete search history.

(56) References Cited

U.S. PATENT DOCUMENTS

| | | | | |
|---|---|---|---|---|
| 2016/0230185 A1* | 8/2016 | Baum | ................ | C12N 15/8286 |
| 2016/0244779 A1* | 8/2016 | Bell | .................. | C12N 15/8261 |

FOREIGN PATENT DOCUMENTS

| | | | |
|---|---|---|---|
| CN | 101045728 A | * | 10/2007 |
| CN | 102409050 A | | 4/2012 |
| CN | 107603984 A | | 1/2018 |
| EP | 3174982 A1 | | 6/2017 |
| WO | WO 2007/035650 A2 | | 3/2007 |
| WO | WO 2016/018887 A1 | | 7/2015 |
| WO | WO 2017/132330 A1 | | 8/2017 |
| WO | WO 2018/026773 A1 | | 2/2018 |

OTHER PUBLICATIONS

Zhu et al (Pest Manag Sci, 2011, 67: 175-182).*
Isoe et al (PNAS, 2011, 108(24): e211-e217).*
Eugsteretal (Molecular Biology of the Cell, 2004, 15: 1011-1023).*
Mao et al (Pesticide Biochemistry and Physiology, 2015, 118: 71-76).*
Evidentiary BLAST search (accessed Apr. 2022).*
Genbank, "Predicted: Aethina tumida coatomer subunit beta' (LOC109598478), mRNA", GenBank:XM_020014388.1, 2017.
Alamalakala et al., "Insect RNAi: Integrating a New Tool in the Crop Protection Toolkit" In: "Trends in Insect Molecular Biology and Biotechnology", Springer International Publishing, 2018, pp. 193-232.
Zhang et al., "Feasibility, limitation and possible solutions of RNAi-based technology for insect pest control", Insect Science, 2013, 20: 15-30.
Zhang et al., "Evolutionary history of Coleoptera revealed by extensive sampling of genes and species", Nature Communications, 2018, 9:205, 11 pages.
Zhang et al., "Negligible transcriptome and metabolome alterations in RNAi insecticidal maize against Monolepta hieroglyphica", Plant Cell Reports, 2020, 39: 1539-1547.

* cited by examiner

*Primary Examiner* — Cathy Kingdon Worley
(74) *Attorney, Agent, or Firm* — James S. Keddie; Bozicevic, Field & Francis LLP

(57) ABSTRACT

Provided are an isolated polynucleotide and a method for controlling insect invasion. The isolated polynucleotide is a plurality of target sequences for controlling target gene c35112 of a coleopteran pest, *Monolepta hieroglyphica*, comprising: a) a polynucleotide sequence shown as SEQ ID NO: 1; or (b) a polynucleotide sequence having at least 15 or 17 or 19 or 21 contiguous nucleotides of SEQ ID NO: 1, a double-stranded RNA comprising at least one strand complementary to the polynucleotide sequence being capable of inhibiting the growth of coleopteran pests after being ingested by the coleopteran pests; or (c) any one of polynucleotide sequences shown as SEQ ID NO: 3 to SEQ ID NO: 20; or (d) a polynucleotide sequence that hybridizes under stringent conditions to a polynucleotide sequence as defined in (a), (b) or (c).

22 Claims, 1 Drawing Sheet

Specification includes a Sequence Listing.

POLYNUCLEOTIDE AND METHOD FOR CONTROLLING INSECT INVASION

CROSS-REFERENCE TO RELATED APPLICATIONS

Figure 1:
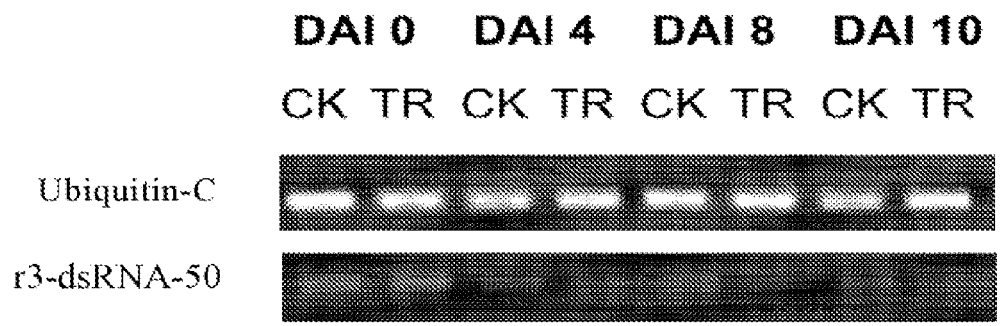

This application is a § 371 national phase of International Application No. PCT/CN2019/085800, filed on May 7, 2019, which claims the benefit of Chinese Application No. 201810550207.4, filed on May 31, 2018, which applications are incorporated by reference herein.

TECHNICAL FIELD

The present invention relates to the field of plant protection, especially crop protection. In particular, the present invention relates to a polynucleotide and method for controlling insect invasion, and especially to a method for controlling the invasion of *Monolepta hieroglyphica* (Motschulsky) by reducing or shutting down the expression of target sequence in the *Monolepta hieroglyphica* by using RNAi technology.

BACKGROUND

Crops are usually the target of insects. In the past few decades, there have been some substantial advances in the development of more effective methods and compositions against insect attack in crops. For example, chemical insecticides, microbial insecticides and genetic engineering methods are used to control harmful insects.

Chemical insecticides are relatively effective means to control the invasion of harmful insects. However, the use of chemical pesticides also has many disadvantages. First of all, chemical insecticides are non-selective. People intend to use chemical insecticides to control insects that are harmful to many crops and other plants. However, due to their lack of selectivity, chemical insecticides are also be harmful to non-target organisms, such as earthworms. In addition, after a period of application of chemical pesticides, they usually make the fields barren. Chemical pesticides exist persistently in the environment and are usually slowly metabolized. This slow metabolism causes the residue of chemical pesticides in crops and the environment, so that they may accumulate in the food chain, especially the food chain of higher carnivores. The accumulation of these chemical pesticides may induce diseases in higher-end species, such as cancers in human. For *Monolepta hieroglyphica*, it survives the winter as egg in the soil, and the larvae also live in the soil after hatching in June of the following year. However, due to the large-scale popularization of straw returning to the field in recent years, the difficulty of using chemical pesticides to control *Monolepta hieroglyphica* is increasing year by year. Especially, from the end of July to the beginning of August, the adult of *Monolepta hieroglyphica* is unearthed and the maize has grown tall at this time, it is even more difficult to apply chemical pesticides for pest control.

Microbial insecticides, especially insecticides obtained from *Bacillus thuringiensis* (Bt) strains, as substitutes for chemical insecticides, have played an important role in agricultural production, and show certain insecticidal activity against insects such as Lepidoptera, Diptera and Coleoptera. However, microbial insecticides have relatively high requirements for the application environment. If the environment is not suitable for the growth of these microorganisms, repeated application is required in production, and in some cases, even repeated application cannot achieve the purpose of controlling pests, which greatly increases production costs.

One or more genes encoding Bt insecticidal protein are transferred into plants through genetic engineering, and some transgenic plants with enhanced pest resistance can be obtained. For example, maize and cotton plants that have been genetically engineered to produce Cry toxins have been widely used in agricultural production in the United States, and provide farmers with an alternative of traditional pest control methods. However, the currently developed genetically modified crops containing Cry toxin can only be used to control relatively narrow range of coleopteran pests, such as corn rootworm and Colorado potato beetle. For one of the main maize pests, *Monolepta hieroglyphica*, there is no report about the application of Cry toxin for prevention and treatment thereof.

In view of the limitations of the above methods, there is an urgent need for a method to control or eradicate insect attack in crop production, especially invasion of *Monolepta hieroglyphica*, which is environmentally friendly (i.e., selective, environmentally friendly, and biodegradable) and can be well used in the pest resistance management system.

RNA interference or RNAi is a method used to down-regulate gene expression in a sequence-specific manner in a cell or whole organism environment. It can achieve the purpose of targeted interference with target gene expression through specific targeted selection and efficient mRNA suppression. Although the use of RNAi technology for pest control is known in the art, in view of the wide variety of insects, not only does this technology have very different effects in different insects, but also the key factor in using this technology as a measure to control insect invasion is to select the most appropriate target genes, that is, those genes whose loss of function leads to serious destruction of essential biological processes and/or death of organisms. Therefore, the present invention uses down-regulation of specific target genes in pests as a means to control insect invasion, especially to control insect invasion in plants.

SUMMARY

The objective of the present invention is to provide a polynucleotide and method for controlling invasion of an insect, that is, using RNAi technology to down-regulate the expression of a target gene: weakening the ability of insect to survive, grow, reproduce, colonize in a specific environment and/or invade a host, so as to achieve the control of insect invasion and damage caused thereby.

In order to achieve the above objective, the present invention provides an isolated polynucleotide, wherein the polynucleotide is selected from:

(a) a polynucleotide sequence as shown in SEQ ID NO:1; or (b) a polynucleotide sequence of at least 15 consecutive nucleotides of SEQ ID NO: 1, wherein when a coleopteran insect pest ingests a double-stranded RNA comprising at least one strand complementary to the polynucleotide sequence, the growth of the coleopteran insect pest is inhibited; or (c) a polynucleotide sequence of at least 17 consecutive nucleotides of SEQ ID NO: 1, wherein when a coleopteran insect pest ingests a double-stranded RNA comprising at least one strand complementary to the polynucleotide sequence, the growth of the coleopteran insect pest is inhibited; or (d) a polynucleotide sequence of at least 19 consecutive nucleotides of SEQ ID NO: 1, wherein when a coleopteran insect pest ingests a double-stranded RNA comprising at least one strand complementary to the polynucleotide sequence, the growth of the coleopteran insect pest is inhibited; or (e) a polynucleotide sequence of at least 21 consecutive nucleotides of SEQ ID NO: 1, wherein when a coleopteran insect pest ingests a double-stranded RNA comprising at least one strand complementary to the polynucleotide sequence, the growth of the coleopteran insect pest is inhibited; or (f) any one of polynucleotide sequences as shown in SEQ ID NOs: 3 to 20; or (g) a polynucleotide sequence that hybridizes or is complementary to a polynucleotide sequence as defined in any one of (a) to (f) under a stringent condition.

Further, the polynucleotide also comprises a complementary sequence of the polynucleotide sequence.

Furthermore, the polynucleotide also comprises a spacer sequence.

Preferably, the spacer sequence is SEQ ID NO:23.

In embodiments based on the above technical solutions, the coleopteran insect pest is *Monolepta hieroglyphica*.

In order to achieve the above objective, the present invention also provides an expression cassette, comprising the polynucleotide sequence under the control of an operatively linked regulatory sequence.

In order to achieve the above objective, the present invention also provides a recombinant vector comprising the polynucleotide sequence or the expression cassette.

In order to achieve the above objective, the present invention also provides a use of the polynucleotide for interfering with the expression of a target sequence of a coleopteran insect pest or inhibiting the growth of a coleopteran insect pest.

In order to achieve the above objective, the present invention also provides an interfering ribonucleic acid, in which after the interfering ribonucleic acid is ingested by a coleopteran insect pest, it down-regulates the expression of at least one target gene in the coleopteran insect pest, wherein the interfering ribonucleic acid comprises at least one silencing element, wherein the silencing element is a double-stranded RNA region comprising annealed complementary strands, wherein one strand comprises or consists of a nucleotide sequence that is at least partially complementary to a target sequence in the target gene, and the target gene comprises the polynucleotide sequence.

Further, the silencing element comprises or consists of a sequence of at least 15 consecutive nucleotides that is at least partially complementary to a target fragment in the target sequence.

Further, the silencing element comprises or consists of a sequence of at least 17 consecutive nucleotides that is at least partially complementary to a target fragment in the target sequence.

Further, the silencing element comprises or consists of a sequence of at least 19 consecutive nucleotides that is at least partially complementary to a target fragment in the target sequence.

Further, the silencing element includes or consists of a sequence of at least 21 consecutive nucleotides that is at least partially complementary to a target fragment in the target sequence.

Alternatively, the interfering ribonucleic acid comprises at least two silencing elements, and each of the silencing elements comprises or consists of a nucleotide sequence that is at least partially complementary to a target sequence in the target gene.

Further, each of the silencing elements comprises or consists of a different nucleotide sequence complementary to a different target sequence.

Further, the different target sequence is derived solely from the target gene or derived from a further target gene different from the target gene.

The further target gene different from the target gene is derived from the same coleopteran insect pest or from a different coleopteran insect pest.

Preferably, the coleopteran insect pest is *Monolepta hieroglyphica*.

In embodiments based on the above technical solutions, the interfering ribonucleic acid further comprises a spacer sequence.

Specifically, the spacer sequence is SEQ ID NO:23.

In order to achieve the above objective, the present invention also provides a composition for controlling an invasion of a coleopteran insect pest, comprising at least one of the interfering ribonucleic acids and at least one suitable carrier, excipient or diluent.

Further, the composition comprises a host cell that expresses or is capable of expressing the interfering ribonucleic acid. Specifically, the host cell is a bacterial cell.

Furthermore, the composition is a solid, liquid or gel. Specifically, the composition is an insecticidal spray.

Optionally, the composition further comprises at least one insecticide, in which the insecticide is a chemical insecticide, potato tuber specific protein, *Bacillus thuringiensis* insecticidal protein, *Xenorhabdus ehlersii* insecticidal protein, *Photorhabdus luminescens* insecticidal protein, *Bacillus laterosporus* insecticidal protein or *Bacillus sphaericus* insecticidal protein.

In order to achieve the above objective, the present invention also provides a use of the composition for controlling an invasion of a coleopteran insect pest for preventing and/or controlling the invasion of the coleopteran insect pest.

Preferably, the coleopteran insect pest is *Monolepta hieroglyphica*.

In order to achieve the above objective, the present invention also provides a method for controlling an invasion of a coleopteran insect pest, comprising contacting the coleopteran insect pest with an effective amount of at least one of the interfering ribonucleic acid sequences.

In order to achieve the above objective, the present invention also provides a method for improving plant resistance to a coleopteran insect pest, comprising introducing the polynucleotide or the expression cassette or the recombinant vector or a construct comprising the interfering ribonucleic acid into the plant.

In order to achieve the above objective, the present invention also provides a method for producing a plant for controlling a coleopteran insect pest, comprising introducing the polynucleotide or the expression cassette or the recombinant vector or a construct comprising the interfering ribonucleic acid into the plant.

In order to achieve the above objective, the present invention also provides a method for protecting a plant from damage caused by a coleopteran insect pest, comprising introducing the polynucleotide or the expression cassette or the recombinant vector or a construct comprising the interfering ribonucleic acid into the plant, wherein the introduced plant inhibits the growth of the coleopteran insect pest after being ingested by the coleopteran insect pest.

In embodiments based on the above technical solutions, the plant is soybean, wheat, barley, maize, tobacco, rice, rape, cotton or sunflower.

The present invention comprises a method for regulating or inhibiting the expression of one or more target genes in a coleopteran insect pest, the method comprising: introducing a part or whole of a stabilized double-stranded RNA (e.g., dsRNA) or a modified form thereof (e.g., small interfering RNA sequence) into a cell or extracellular environment of an invertebrate harmful insect. In the body of the insect, the dsRNA or siRNA enters cells to inhibit the expression of at least one or more target genes, and this inhibition reduces the insect's ability to survive, grow, reproduce, and invade the host.

DETAILED DESCRIPTION

Hereinafter, various aspects of the present invention will be described in detail.

*Monolepta hieroglyphica* and its Damage to Crops

The *Monolepta hieroglyphica* (Motschulsky) of the present invention is a holometabolous insect of Galeruca, Chrysomelidae, Coleoptera. Its egg, larvae and pupae live in the soil, and its adult flies out of the soil after eclosion. It is a yearly insect, and overwinters with diapause eggs. Diapause eggs start to hatch in May each year, and larvae can be observed in the field soil from May to early July; pupae can be seen in the field from the end of June to mid-July; adults emerge occasionally and fly into maize, soybean and other fields to cause damage; the peak period of eclosion is from the end of July to the beginning of August; about 15 days after eclosion, spawning can begin, and the spawning period lasts about 1 month.

The larvae of *Monolepta hieroglyphica* mainly feed on the roots of crops in the field, and the damage of larvae is not reflected in parts above ground; each year in mid-July, the adults can be found to damage the leaves in maize and soybean fields; a large number of adults mainly damage maize filaments from the end of July to the beginning of August, in which the maize filaments are bitten off, which seriously affects pollination, resulting in pointed and spindle-shaped ears, thereby causing reduction of maize production; subsequently, *Monolepta hieroglyphica* move to soybean fields to feed on soybean leaves, or move to surrounding vegetable fields to harm vegetables. From 2009 to 2016, in China, the area of maize harmed by *Monolepta hieroglyphica* increased from 16 million mu times to nearly 40 million mu times, and the occurrence area doubled. And the area of damage also spread from the northwest and other places to the major maize production areas such as northeast and north China.

At the same time, with the continuous advancement of straw returning measures, the continuous enrichment of field humus and the increase of soil surface cover make it more difficult to apply pesticides to the soil, and the prevention and control of *Monolepta hieroglyphica* larvae becomes more and more difficult. That is to say, the natural protection provided by the straw returning to the larvae of *Monolepta hieroglyphica* may greatly increase the survival rate of the larvae of *Monolepta hieroglyphica*, thereby causing the increase of population density of *Monolepta hieroglyphica*. The adults of *Monolepta hieroglyphica* are good flying and jumping insects, and begin to damage maize after eclosion from mid-to-late July when maize enters silking period. At this time, maize has grown taller, the difficulty of applying pesticides increases, and it is easy to cause tragedy that pesticides accidentally injure the sprayers. At the same time, their non-selective insecticidal effects may cause damage to crops and non-target organisms. In addition, chemical pesticides may have a cumulative effect in the human body and become mutagens or carcinogens. Therefore, it is necessary to have a precise, environmentally friendly, and easy-to-operate method for farmers to control the damage of *Monolepta hieroglyphica*. Through genetic modification, the crop has a certain anti-insect effect during the entire growth period, and the protection for the whole plant and the entire growth period are achieved.

Based on the above problems, it is one of the best solutions to use a genetically modified RNAi method to control *Monolepta hieroglyphica* and to provide prevention and control for full growth period and whole plant in maize, soybeans and other crops.

RNAi and Polynucleotide Sequence

The present invention relates generally to RNAi technology. In the present invention, "RNA interference (RNAi)" refers to that some RNA can efficiently and specifically block the expression of specific genes in vivo, promote mRNA degradation, and induce cells to show the phenotype of specific gene deletion. It is also called RNA intervention or interference. RNA interference is a highly specific gene silencing mechanism at mRNA level.

In the present invention, RNA interference or RNAi is used to down-regulate gene expression. RNAi is a method of sequence-specific gene regulation typically mediated by a double-stranded RNA molecule (such as siRNA). The siRNA comprises a sense RNA strand that is annealed by complementary base pairing with an antisense RNA strand. The sense strand or "guide strand" of the siRNA molecule comprises a nucleotide sequence that is complementary to a nucleotide sequence located in an RNA transcript of the target gene. Therefore, the sense strand of siRNA can be annealed with the RNA transcript through Watson-Crick-type base pairing, and target to the RNA so as to degrade in a cell complex called RNAi-induced silencing complex or RISC.

The present invention provides an isolated and purified polynucleotide, which sequence is shown in SEQ ID NO: 1. The present invention also provides any RNA, including dsRNA, expressed from the polynucleotide. The present invention provides a stabilized double-stranded RNA molecule for inhibiting the expression of a target sequence by a coleopteran pest. When expressed as a dsRNA and provided to a pest, the fragment can be defined as a fragment that causes the pest to die, inhibit feeding, block or stop. The fragment may, for example, comprise at least about 19, 21, 23, 25, 40, 60, 80, 100, 125 or more consecutive nucleotides, or about 19 to about 100 or more nucleotides of SEQ ID NO: 1 or its complementary sequence, such as SEQ ID NOs: 3 to 20. A dsRNA sequence comprising about 19 to 300 nucleotides that are homologous to the pest target sequence is particularly useful.

The stabilized double-stranded RNA comprises at least two coding sequences, which are arranged in sense and antisense directions relative to at least one promoter, wherein the nucleotide sequences comprising the sense strand and the antisense strand are ligated through a spacer sequence of at least about 5 to 1000 nucleotides, wherein the sense strand and the antisense strand may be of different lengths, and wherein at least one of the two coding sequences has a sequence identity of at least 80%, at least 90%, at least 95%, at least 98%, or 100% to the nucleotide sequence shown in SEQ ID NO: 1.

The term "control of insect" or "control of pest" or "control of insect pest" in the present invention refers to any effect that can restrict the damage caused by an insect and act on the insect, including but not limited to killing insect, inhibiting insect development, changing the reproduction or growth of an insect in such a way that the insect provides less damage to a plant, reducing the number of offspring produced by an insect, producing fewer normal insects, producing an insect that is more vulnerable to a predator, or preventing an insect from eating a plant.

The "target gene" described in the present invention is any sequence that is intended to be down-regulated in an insect. The invasion of insect is controlled by down-regulating the target gene, such as via destroying an essential biological process in the insect. Therefore, the preferred target gene includes, but is not limited to, a gene that plays a key role in regulating feeding, survival, growth, development, reproduction, invasion and infection. When the expression of the target gene is down-regulated or inhibited, at least 30% of insects are killed; or at least 30% of insects are prevented/delayed/hampered/retarded/impeded from growth, or at least 30% of insects are prevented from reproduction, or at least 30% of insects are prevented from transitioning through life cycle; or the damage caused by insects and/or the ability of insects to infect or invade the environment, surfaces, and/or plant or crop species are reduced; or at least 30% of insects stop eating their natural food resources (such as plants and plant products). These target genes can be expressed in all or part of insect cells. In addition, these target genes can be expressed only in a specific stage of insect life cycle, such as adult stage or larval stage or egg stage.

In the present invention, the term "pest" is preferably an insect that causes plant invasion/harassment/infestation, and belongs to Coleoptera, preferably *Monolepta hieroglyphica*. The terms "infestation", "harassment" and/or "invasion" are generally used interchangeably in the present disclosure.

In the present invention, "nucleic acid" refers to a single- or double-stranded polymer of deoxyribonucleic acid or ribonucleic acid bases that are read from 5' to 3' end. Optionally, "nucleic acid" may also comprise non-naturally occurring or altered bases, which allow correct reading by polymerase without reducing the expression of polypeptide encoded by the nucleic acid. "Nucleotide sequence" refers to sense and antisense strands of nucleic acid that exist as a separate single-strand or that exist in a duplex. "Ribonucleic acid" (RNA) comprises RNAi (RNA interference), dsRNA (double-stranded RNA), siRNA (small interfering RNA), mRNA (messenger RNA), miRNA (microRNA), tRNA (transfer RNA, which is or is not charged by a corresponding acylated amino acid), cDNA, genomic DNA and DNA-RNA hybrid. "Nucleic acid fragment", "nucleic acid sequence fragment" or more commonly "fragment" will be understood by those skilled in the art as: comprising genomic sequence, ribosomal RNA sequence, transfer RNA sequence, messenger RNA sequence, operon sequence, and smaller engineering modified nucleotide sequence, in which the sequence expresses or can be modified to express protein, polypeptide or peptide.

The "interfering ribonucleic acid" of the present invention covers any type of RNA molecule that can down-regulate or "silence" the expression of a target gene, including but not limited to sense RNA, antisense RNA, siRNA, miRNA, dsRNA, hairpin RNA, etc. Methods for determining functional interfering RNA molecules are well known in the art and have been disclosed.

The interfering ribonucleic acid of the present invention can specifically down-regulate the expression of a target gene by binding to a target sequence in the target gene. The binding occurs because of the base pairing between the interfering RNA and a complementary region of the target sequence.

In addition, the present invention encompasses nucleic acid molecules or fragments thereof that hybridize (especially specifically hybridize) with the polynucleotide of the present invention under "stringent conditions". As those skilled in the art know, nucleic acid molecules or fragments thereof can specifically hybridize with other nucleic acid molecules under certain conditions. In the present invention, if two nucleic acid molecules can form an anti-parallel double-stranded nucleic acid structure, it can be said that the two nucleic acid molecules can specifically hybridize with each other. If two nucleic acid molecules show complete complementarity, it can be said that one of the nucleic acid molecules is a "complement" of the other nucleic acid molecule. In the present invention, when each nucleotide of one nucleic acid molecule is complementary to the corresponding nucleotide of another nucleic acid molecule, it is said that the two nucleic acid molecules show "complete complementarity". If two nucleic acid molecules can hybridize to each other with sufficient stability so that they can be annealed and bind to each other under at least conventional "lowly stringent" conditions, it can be said that the two nucleic acid molecules are "minimally complementary". Similarly, if two nucleic acid molecules can hybridize to each other with sufficient stability so that they can be annealed and bind to each other under conventional "highly stringent" conditions, it can be said that the two nucleic acid molecules have "complementarity". Deviation from complete complementarity is permissible, as long as the deviation does not completely prevent the two molecules from forming a double-stranded structure. In order for a nucleic acid molecule to act as a primer or probe, it is only necessary to ensure that it has sufficient complementarity in sequence, so that a stable double-stranded structure can be formed under the used specific solvent and salt concentration. In the present invention, a substantially homologous sequence is a nucleic acid molecule that can specifically hybridize with the complementary strand of another matched nucleic acid molecule under highly stringent conditions. Suitable stringent conditions to promote DNA hybridization comprises, for example, treating with 6.0× sodium chloride/sodium citrate (SSC) at approximately 45° C., and then washing with 2.0×SSC at 50° C., and these conditions are well known to those skilled in the art. For example, the salt concentration in the washing step can be selected from about 2.0×SSC, 50° C. under lowly stringent conditions to about 0.2×SSC, 50° C. under highly stringent conditions. In addition, the temperature conditions in the washing step can be raised from room temperature of about 22° C. under lowly stringent conditions to approximately 65° C. under highly stringent conditions. The temperature conditions and the salt concentrations can both change, or one of them can remain unchanged while the other variable changes. Preferably, the stringent conditions of the present invention can be that specific hybridization with the polynucleotide of the present invention is carried out in 6×SSC, 0.5% SDS solution at 65° C., and then the washing is carried out once by using each of 2×SSC, 0.1% SDS and 1×SSC and 0.1% SDS.

The term "silencing element" refers to a portion or region of an interfering ribonucleic acid that comprises or consists of a nucleotide sequence complementary or at least partially complementary to a target sequence in a target gene, and the portion or region acts as an active portion of the interfering ribonucleic acid so as to direct the down-regulation of the target gene expression. The silencing element comprises an interfering ribonucleic acid that comprises or consists of at least 15 consecutive nucleotides, preferably at least 18 or 19 consecutive nucleotides, more preferably at least 21 consecutive nucleotides, even more preferably at least 22, 23, 24 or 25 consecutive nucleotides that are complementary to the target sequence in the target gene. In the case of the preferred interfering ribonucleic acid of the present invention, the silencing element may be a double-stranded region containing annealed a complementary strand, wherein at least one strand comprises an interfering ribonucleic acid that comprises or consists of a nucleotide sequence complementary or at least partially complementary to the target sequence in the target gene. The double-stranded region has a length of at least about 15 to about 25 base pairs, or a length of about 25 to about 100 base pairs, or even a length of about 3000 base pairs.

In the present invention, "target gene expression" refers to the transcription and accumulation of an RNA transcript encoded by a target gene, and/or the translation of mRNA into protein.

The term "down-regulation" refers to any one of the methods known in the art for an interfering ribonucleic acid to reduce the level of a primary RNA transcript, mRNA or protein produced by a target gene. The down-regulation refers to a situation whereby the level of RNA or protein produced by a gene is reduced by at least 10%, preferably at least 33%, more preferably at least 50%, even more preferably at least 80%. In particular, down-regulation refers a situation whereby the level of RNA or protein produced by a gene in insect cells is reduced by at least 80%, preferably at least 90%, more preferably at least 95%, and most preferably at least 99%, as compared with appropriately controlled insects (for example, insects that have not been exposed to the interfering ribonucleic acid or have been exposed to a control interfering ribonucleic acid). Methods for detecting the reduction of RNA or protein level are well known in the art, and comprise RNA solution hybridization, Northern hybridization, reverse transcription (e.g., quantitative RT-PCR analysis), microarray analysis, antibody binding, and enzyme-linked immunosorbent assay (ELISA) and Western blotting. At the same time, down-regulation can also refer to that the level of RNA or protein is reduced enough to cause a detectable change in insect phenotype, such as cell death, growth arrest, etc., as compared with a proper insect control. Therefore, conventional techniques in the art can be used to measure down-regulation through phenotypic analysis of insects.

In the present invention, "inhibition of target gene expression" refers to the decrease or absence (below the detectable threshold) of a protein and/or mRNA product level of a target gene. Specificity refers to the ability to inhibit a target gene without affecting other genes in a cell and to have no effect on any gene in the cell that produces dsRNA molecules.

In the present invention, "sense" RNA refers to an RNA transcript corresponding to a sequence or fragment that exists in the form of mRNA that can be translated into protein by a plant cell. In the present invention, "antisense" RNA refers to an RNA that is complementary to all or part of a mRNA normally produced in a plant. The complementation of antisense RNA can be directed to any part of a specific gene transcript, i.e. 5' non-coding sequence, 3' non-coding sequence, intron or coding sequence. In the present invention, "RNA transcript" refers to a transcription product of a DNA sequence catalyzed by an RNA polymerase. When an RNA transcript is a completely complementary copy of a DNA sequence, it is called a primary transcript, or it may be an RNA obtained by post-transcriptional processing of a primary transcript and thus is called a mature RNA.

In the present invention, dsRNA molecules can serve as precursors of active siRNA molecules, and these siRNA molecules guide RNA transcripts to RISC complexes for subsequent degradation. A dsRNA molecule present in an organism or its surrounding environment can be taken up by the organism and processed by an enzyme called DICER to obtain a siRNA molecule. Alternatively, the dsRNA molecule can be produced in vivo, that is, it is transcribed from one or more polynucleotides encoding the dsRNA that exists in a cell (such as a bacterial cell or a plant cell), and after ingesting a longer precursor dsRNA, it is processed by DICER in a host cell or preferably an insect cell. The dsRNA can be formed from two separate (sense and antisense) RNA strands that are annealed by means of complementary base pairing. Alternatively, the dsRNA may be a single strand, which can refold on itself to form a hairpin RNA or stem loop structure. In the case of one RNA strand, the double-stranded region or "stem" is formed by two regions or segments of the RNA, and these regions or segments are basically inverted repeat sequences of each other and have sufficient complementarity to allow the formation of a double-stranded region. There may be one or more functional double-stranded silencing elements in this "stem region" of the molecule. The inverted repeat region is typically separated by a region or segment called "loop" region in the RNA. This region may contain any nucleotide sequence that confers sufficient flexibility to allow self-pairing between the flanking complementary regions of the RNA. In general, the loop region is essentially single-stranded and acts as a spacer between the inverted repeat sequences.

The interfering ribonucleic acid in the present invention comprises at least one double-stranded region, which is typically a silencing element of the interfering ribonucleic acid. It comprises a sense RNA strand annealed by complementary base pairing with an antisense RNA strand, wherein the sense strand of dsRNA molecule comprises a nucleotide sequence that is complementary to a nucleotide sequence located in an RNA transcript of a target gene. The silencing element or at least one strand thereof (when the silencing element is double-stranded) may be completely complementary or partially complementary to a target sequence of the target gene. The term "completely complementary" means that all bases of the silencing element nucleotide sequence are complementary or "matched" to the bases of the target sequence. The term "at least partially complementary" means that less than 100% of the bases of the silencing element and the bases of the target sequence are matched. Those skilled in the art will understand that in order to mediate the down-regulation of target gene expression, the silencing element only needs to be at least partially complementary to the target sequence. It is known in the art that an RNA sequence with an insertion, deletion and mismatch relative to the target gene can still be effective in terms of RNAi. Preferably, the silencing element and the target sequence of the target gene have a sequence identity of at least 80% or 85%, preferably a sequence identity of at least 90% or 95%, or more preferably a sequence identity of at least 97% or 98%, and even more preferred a sequence identity of at least 99%. Alternatively, the silencing element may contain 1, 2 or 3 mismatches over each length of 24 partially complementary nucleotides, as compared to the target sequence. It is well known to those skilled in the art that the degree of complementarity shared between the silencing element and the target sequence varies depending on the insect species in which the expression of target gene to be down-regulated is to be controlled.

The target sequence in the present invention can be selected from any suitable region or nucleotide sequence of the target gene or its RNA transcript. For example, the target sequence can be located within the 5' UTR or 3' UTR of the target gene or RNA transcript, or within the exon or intron region of the gene.

The interfering ribonucleic acid of the present invention may comprise one or more silencing elements, wherein each silencing element comprises or consists of a nucleotide sequence that is at least partially complementary to the target sequence in the target gene, and acts to down-regulate the expression of the target gene after being ingested by an insects. The term "plurality" means at least two, at least three, at least four, etc., and up to at least 10, 15, 20, or at least 30. The interfering ribonucleic acid comprises a plurality of copies of a single silencing element, that is, the repetition of a silencing element that binds to a specific target sequence within a specific target gene. The silencing element within the interfering ribonucleic acid can also comprise or consist of different nucleotide sequences complementary to different target sequences. It should be clear that the combination of a plurality of copies of same silencing element combined with silencing elements that bind to different target sequences is also within the scope of the present invention.

In order to achieve the down-regulation of a specific target gene in a coleopteran insect in the present invention, different target sequences can be derived from a single target gene in one insect. In this case, the silencing element in the interfering ribonucleic acid can be combined in the original order in which the target sequence exists in the target gene, or as compared with the order of the target sequence in the target gene, the silencing element can be disrupted in the environment of the interfering ribonucleic acid and combined randomly in any rank order.

Alternatively, different target sequences represent a single target gene, but are derived from different insect species.

Alternatively, different target sequences can be derived from different target genes. If the interfering ribonucleic acid is used to prevent and/or control pest invasion, it is preferable that the different target genes are selected from the group of genes that regulate essential biological functions of insects, and these biological functions include but are not limited to survival, growth, development, reproduction and pathogenicity. Target genes can regulate the same or different biological pathways or processes.

In the present invention, different genes targeted by different silencing elements are derived from the same insect. This method can be used to achieve an enhanced attack against a single insect. Specifically, different target genes can be differentially expressed in different stages of the insect life cycle, such as the mature adult stage, the immature larval stage, and the egg stage. Therefore, the interfering ribonucleic acid of the present invention can be used to prevent and/or control insect invasion during more than one stage of the insect life cycle. Alternatively, different genes targeted by different silencing elements are derived from different insects. Therefore, the interfering ribonucleic acid of the present invention can also be used to prevent and/or control the invasion of more than one insect at the same time.

The silencing element in the present invention can be a consecutive region of the interfering ribonucleic acid or can be separated by the presence of a linker sequence. The linker sequence may comprise a short random nucleotide sequence that is not complementary to any target sequence or the target gene. The linker sequence may be a conditionally self-cleaving RNA sequence, preferably a pH-sensitive linker or a hydrophobic-sensitive linker. The linker may also comprise a nucleotide sequence equivalent to an intron sequence. The linker sequence may have a length ranging from 1 base pair to about 10000 base pairs, provided that the linker does not impair the ability of interfering ribonucleic acid to down-regulate gene expression.

In addition to one or more silencing elements and any linker sequences, the interfering ribonucleic acid of the present invention may also comprise at least one additional polynucleotide sequence. The additional polynucleotide sequence is selected from (1) a sequence capable of protecting the interfering ribonucleic acid from RNA processing; (2) a sequence affecting the stability of the interfering ribonucleic acid; (3) a sequence allowing protein binding to promote the ingestion of the interfering ribonucleic acid by an insect cell; (4) a sequence capable of promoting large-scale production of the interfering ribonucleic acid; (5) a sequence that acts as an aptamer capable of binding to a receptor or molecule on the surface of an insect cell to promote ingestion; or (6) a sequence capable of catalyzing the processing of the interfering ribonucleic acid in an insect cell and thereby enhancing the effectiveness of the interfering ribonucleic acid.

The length of the interfering ribonucleic acid of the present invention needs to be enough to be ingested by an insect cell and to down-regulate the target gene of the insect. The upper limit of the length may depend on (1) the requirement for ingestion of the interfering ribonucleic acid by an insect cell, and (2) the requirement for processing of the interfering ribonucleic acid in an insect cell so as to mediate gene silencing through the RNAi pathway; and the length may also be determined by the production methods and the formulations for delivering the interfering ribonucleic acid into an cell. Preferably, the length of the interfering ribonucleic acid of the present invention may be between 19 and 10000 nucleotides, preferably between 50 and 5000 nucleotides, or between 100 and 2500 nucleotides, and more preferably between 80 and 2000 nucleotides.

The interfering ribonucleic acid of the present invention may comprise DNA bases, non-natural bases or non-natural backbone linkages or modifications of saccharide-phosphate backbones, for example, to enhance stability during storage or enhance resistance to nuclease degradation. In addition, the interfering ribonucleic acid can be produced by a person of ordinary skill in the art in a chemical or enzymatic method through manual or automatic reaction. Alternatively, the interfering ribonucleic acid may be transcribed from a polynucleotide encoding it. Therefore, the present invention provides any one of isolated polynucleotides encoding the interfering ribonucleic acid.

The polynucleotide of the present invention can be inserted into a DNA construct or vector known in the art by conventional molecular cloning techniques. The DNA construct can be a recombinant DNA vector, such as a bacterial, viral or yeast vector. The DNA construct is an expression construct, and the polynucleotide is operably linked to at least one regulatory sequence capable of driving the expression of the polynucleotide sequence. The term "regulatory sequence" refers to any nucleotide sequence capable of affecting the expression of an operably linked polynucleotide, including but not limited to promoters, enhancers, and other naturally occurring or synthetic transcriptional activation elements. The regulatory sequence can be located at the 5' or 3' end of the polynucleotide sequence. The term "operably linked" refers to that the regulatory sequence and the polynucleotide sequence are a functionally linked between each other, and such linkage allows the regulatory sequence to drive the expression of the polynucleotide. The operably linked elements may be consecutive or inconsecutive.

The regulatory sequence in the present invention may be a promoter. Preferably, the promoter is a promoter that can be expressed in a plant, and the "promoter that can be expressed in a plant" refers to a promoter that ensures the expression of a polynucleotide linked thereto in a plant cell. The promoter that can be expressed in a plant may be a constitutive promoter. Examples of promoters that direct constitutive expression in plants include, but are not limited to, 35S promoter derived from cauliflower mosaic virus, maize ubi promoter, rice GOS2 gene promoter, and the like. Alternatively, the promoter that can be expressed in a plant can be a tissue-specific promoter, such as PEP carboxylase promoter, that is, such promoter directs the expression of a coding sequence in some tissues of the plant, such as in green tissues, at a level higher than that in other tissues of the plant (which can be determined by conventional RNA test). Alternatively, the promoter that can be expressed in a plant can be a wound-inducible promoter. The wound-inducible promoter or a promoter that directs a wound-induced expression pattern refers to that when a plant is subjected to mechanical or insect gnawing wounds, the expression of the polynucleotide under the regulation of the promoter is significantly higher than that under normal growth conditions. Examples of wound-inducible promoters include, but are not limited to, promoters of potato and tomato protease inhibitor genes (pin I and pin II) and maize protease inhibitor gene (MPI).

Alternatively, one or more transcription termination sequences may be incorporated into the expression construct of the present invention. The term "transcription termination sequence" encompasses a control sequence at the end of a transcription unit, which transmits signals of transcription termination, 3' processing and polyadenylation of a primary transcript. Additional regulatory elements include, but are not limited to, transcriptional or translational enhancers, which can be incorporated into the expression construct, for example, dual-enhanced CaMV35S promoter.

The method for producing any interfering ribonucleic acid in the present invention comprises the following steps: (1) contacting a polynucleotide encoding the interfering ribonucleic acid or a DNA construct comprising the polynucleotide with a cell-free component; (2) introducing the polynucleotide encoding the interfering ribonucleic acid or the DNA construct comprising the polynucleotide (for example, by transformation, transfection or injection) into a cell.

In the present invention, the host cell comprising any interfering ribonucleic acid of the present invention, any polynucleotide of the present invention, or a DNA construct comprising the polynucleotide may be a prokaryotic cell, including but not limited to Gram-positive and Gram-negative bacterial cells; or an eukaryotic cell, including but not limited to yeast cells or plant cells. Preferably, the host cell is a bacterial cell or a plant cell. The polynucleotide or DNA construct of the present invention can exist or maintain as an extrachromosomal element in the host cell, or can be stably incorporated into the genome of the host cell.

In the present invention, when the interfering ribonucleic acid is expressed in the host cell and/or is used to prevent and/or control insect infestation of the host organism, it is preferable that the interfering ribonucleic acid does not exhibit a significant "off-target" effect, that is, the interfering ribonucleic acid does not affect the expression of non-target genes in the host. Preferably, the silencing gene does not exhibit significant complementarity with a nucleotide sequence other than the established target sequence of the target gene. The silencing element exhibits a sequence identity of less than 30%, more preferably less than 20%, more preferably less than 10%, and even more preferably less than 5%, to any gene of the host cell or organism. If the genome sequence data of the host organism is available, then one can use standard bioinformatics tools to cross-check the consistency with the silencing element. In a region with 17 consecutive nucleotides, more preferably in a region with 18 or 19 consecutive nucleotides, and most preferably in a region with 19 or 20 or 21 consecutive nucleotides, there is no sequence identity between the silencing element and the gene from the host cell or organism.

The nucleotide sequence of the present invention may comprise inverted repeats separated by a "spacer sequence". The spacer sequence may be a region comprising any of the following nucleotide sequences, and if necessary, the nucleotide sequences can promote the formation of secondary structure between each repeat. The spacer sequence is part of the sense or antisense coding sequence used for mRNA. Alternatively, the spacer sequence may comprise any combination of nucleotides or homologs thereof that can be covalently linked to the nucleic acid molecule. The spacer sequence may comprise a nucleotide sequence of at least about 10 to 100 nucleotides in length, or at least about 100 to 200 nucleotides in length, at least about 200 to 400 nucleotides in length, or at least about 200 to 400 nucleotides in length, or about 400 to 500 nucleotides in length.

In the present invention, when the interfering ribonucleic acid is "introduced" into a plant, it means that it can occur through a direct transformation method, such as *Agrobacterium*-mediated transformation, particle bombardment, electroporation, etc., for plant tissues; or can be carried out by crossing a plant having a heterologous nucleotide sequence with another plant so that the progeny have the nucleotide sequence incorporated into their genome. Such breeding techniques are well known to those skilled in the art.

Plants

The plants described in the present invention include but are not limited to soybean, wheat, barley, maize, tobacco, rice, rape, cotton or sunflower. In a specific embodiment, the plant is maize. In another specific embodiment, the plant is soybean.

The plants described in the present invention may comprise any reproductive or propagation material of a plant, and may also comprise plant cells, plant protoplasts, plant tissue cultures, plant callus, and plant cells that are intact in a plant or a part of plant. The "part of plant" includes embryos, pollen, ovules, seeds, leaves, flowers, branches, fruits, pits, ears, cobs, shells, stems, roots, root tips and the like. In a specific embodiment, the "part of a plant" is a leaf, more specifically a leaf blade.

Compositions

In the present invention, the composition for preventing and/or controlling insect infestation comprises at least one interfering ribonucleic acid and optionally at least one suitable carrier, excipient or diluent, wherein the interfering ribonucleic acid down-regulates the expression of a target gene in an insect after it is ingested by the insect. The interfering ribonucleic acid comprises or consists of at least one silencing element, and the silencing element is a double-stranded RNA region comprising annealed complementary strands, wherein one strand (sense strand) comprises a nucleotide sequence that is at least partially complementary to a target sequence in the target gene. The target gene includes, but is not limited to, a gene that regulates insect survival, growth, development, reproduction, and pathogenicity. Optionally, the composition comprises at least one host cell, the host cell comprising at least one interfering ribonucleic acid or a DNA construct encoding the interfering ribonucleic acid, and optionally at least one suitable carrier, excipient or diluent, wherein after the host cell is ingested by an insect, the interfering ribonucleic acid acts to downregulate the expression of the target gene in the insect.

The composition of the present invention can be in any physical form suitable for administration to an insect. For example, the composition may be in solid form (powder, pellet or bait), liquid form (including as an insecticidal spray), or gel form. The composition may be a paint, paste or powder, which may be applied to a substrate in order to protect the substrate from the infestation of insect. The composition can be used to protect any substrate or material that is sensitive to insect attack or damage caused by insect.

The nature of the excipient and the physical form of the composition can vary depending on the nature of the substrate to be treated. For example, the composition may be a liquid, which is coated or sprayed on the material or substrate to be treated, or printed on the material or substrate to be treated; or may be a coating or powder, which is applied to the material or substrate to be treated.

In the present invention, the composition may be in the form of bait. The bait is used to attract an insect to contact the composition. After the insect contacts with it, the composition is then internalized by the insect via, for example, ingestion and mediates RNAi, thereby killing the insect. The bait may comprise a food, such as a protein-based food, such as fish meal. Boric acid can also be used as a bait. The bait may depend on the species to be targeted. An attractant may also be used, for example, the attractant can be a pheromone, such as a male or female pheromone. The attractant functions attracting an insect to contact the composition, and can be targeted to a specific insect or can attract the entire range of insects, increasing the chance of these attracted insects to contact the composition of the present invention, thereby killing a large number of insects. The bait can be in any suitable form, such as solid, paste, pellet or powder form.

Bait can also be brought back to the community by insects. The bait can then serve as a food source for other members of the community, thereby providing an effective control of a large number of insects and potentially the entire insect community. The bait can also be provided in a suitable "housing" or "trap".

In addition, the composition in contact with an insect may remain on the insect's epidermis. When cleaning, whether a single insect cleans itself or insects cleaning each other, these compositions may be ingested and thereby mediating their effects in insects. This requires the composition to be sufficiently stable so that even after exposure to external environmental conditions for a period of time (such as several days), the interfering ribonucleic acid remains intact and can mediate RNAi.

In the present invention, the composition can be provided in the form of a spray. Therefore, human users can directly spray insects with the composition. The composition is then internalized by an insect, where it can mediate RNA interference so as to control the insect. The spray is preferably a pressurized/atomized spray or a pump spray. These particles may be of suitable size so that they adhere to the insect, for example adhere to exoskeleton and can be absorbed from there.

The carrier of the composition in the present invention is a powder or granule charged with static electricity, which adheres to an insect. Optionally, the carrier of the composition may comprise magnetic particles which adhere to insect epidermis. Optionally, the carrier of the composition comprises metal particles, and these particles are initially unmagnetized but capable of becoming magnetically polarized when experiencing an electric field provided by the insect body. Preferably, the composition is incorporated into a carrier, and the carrier increases the ingestion of interfering RNA in an insect. This carrier may be a lipid-based carrier, preferably comprising one or more of the followings: oil-in-water emulsions, micelles, cholesterol, lipopolyamines, and liposomes. Other agents that promote ingestion of the construct of the present invention are well known to those skilled in the art, and include polycations, dextran, and cationic lipids, such as CS096, CS102, and the like. Optionally, the carrier of the composition is a nucleic acid coagulant; preferred nucleic acid coagulants include spermidine or protamine sulfate or derivatives thereof.

In the case where the composition of the present invention is suitable for preventing and/or controlling insect infestation of a plant, the composition may comprise an agriculturally suitable carrier. This carrier may be any material which the plant to be treated can tolerate, this material does not cause undue damage to the environment or other organisms therein, and it allows the interfering ribonucleic acid to remain effective against insects. Specifically, the composition of the present invention can be formulated for delivery to plants according to conventional agricultural practices used in the biopesticide industry. The composition may comprise an additional component capable of performing other functions, including but not limited to (1) enhancing or promoting the ingestion of the interfering ribonucleic acid by an insect cell, and (2) stabilizing an active component of the composition. Such additional component contained in the composition containing the interfering ribonucleic acid may be yeast tRNA or yeast total RNA.

The composition may be formulated for direct application or formulated as a concentrated form of primary composition that should be diluted before use. Alternatively, the composition may be supplied in the form of a kit, the kit comprising the interfering ribonucleic acid in a container or a host cell containing/expressing the interfering ribonucleic acid and a suitable diluent or carrier for the RNA or the host cell in a separate container. In the application of the present invention, the composition can be applied to the plant or any part of the plant at any stage of plant development, for example, the composition is applied to an aerial part of the plant during the cultivation of the plant in the field; and the composition is applied to plant seeds during storage or after planting it in the soil. All in all, it is important to obtain good control of insects in the early stages of plant growth, as this is the period when plants may be most severely damaged by insects.

In the present invention, the composition can be applied to the environment of an insect by different techniques, including but not limited to spraying, atomizing, dusting, spreading, pouring, coating seeds, seed treatment, introduction into soil and introduction into irrigation water. When treating a plant that is susceptible to insect infestation, the composition can be delivered to the plant or part of the plant before the insects appear (for prevention purposes) or after the signs of insect infestation begin to appear (for control purposes).

The composition of the present invention can be formulated to comprise at least one additional active agent. Therefore, the composition can be provided in the form of a "multi-part kit", the kit comprising the interfering ribonucleic acid-containing composition in a container and one or more suitable active ingredients, such as chemical or biological pesticides, in a separate container. Alternatively, the composition may be provided in the form of a mixture that is stable and used in combination with each other.

Suitable active ingredients that can act on the interfering ribonucleic acid of the present invention in a complementary manner include but are not limited to the following: chlorpyrifos, allethrin, resmethrin, tetrabromoethyl, dimethanol-cyclopropanecarboxylic acid (generally contained in a liquid composition); as well as hydramethylnon, avermectin, chlorpyrifos, sulfluramid, hydroprene, fipronil (GABA receptor), isopropylphenylmethyl carbamate, indoxacarb, noviflumuron (chitin synthesis inhibitor), imiprothrin, abamectin (glutamate-gated chloride channel), imidacloprid (acetylcholine receptor) (generally contained in a bait composition). Preferably, in terms of health and environmental considerations, the known active ingredient is an insecticide, such as hydramethylnon and abamectin.

The composition of the present invention can be formulated to contain at least one additional agronomic agent, such as an herbicide or an additional insecticide. "Additional insecticide" or "second insecticide" refers to an insecticide other than the first or original interfering RNA molecule of the composition. Optionally, the composition of the present invention may be delivered in combination with at least one additional agronomic agent (e.g., a herbicide or a second insecticide). The composition can be provided in combination with a herbicide, the herbicide being selected from any herbicide known in the art, such as glyphosate, 2,4-D, imidazolinone, sulfonylurea, and bromoxynil. The composition can also be provided in combination with at least one additional insecticide, and the additional insecticide can be selected from any insecticide known in the art and/or may comprise an interfering ribonucleic acid, and the interfering ribonucleic acid acts to down-regulate the expression of a target gene in an insect after being ingested by the insect. The target pest is an insect and the interfering ribonucleic acid is any one selected from the interfering ribonucleic acids of the present invention. The additional insecticide comprises an interfering ribonucleic acid, which acts to down-regulate the expression of a known gene in any target pest. The original interfering ribonucleic acid and the second or additional insecticide of the composition can target to the same or different insects. For example, the original interfering ribonucleic acid and the second insecticide can target to different insects or can target insects of different families or classes, such as fungi or nematodes or insects. Those of ordinary skill in the art should know how to test the synergistic effect of the interfering ribonucleic acid in combination with other agronomic reagents. Preferably, the composition comprises a first interfering ribonucleic acid and one or more additional insecticides, each of which is toxic to the same insect, wherein the one or more additional insecticides are selected from potato tuber specific protein, *Bacillus thuringiensis* insecticidal protein, *Xenorhabdus ehlersii* insecticidal protein, *Photorhabdus luminescens* insecticidal protein, *Bacillus laterosporus* insecticidal protein, *Bacillus sphaericus* insecticidal protein and lignin. Different components can be delivered simultaneously or sequentially to the area or organism to be treated.

Method for Preventing and/or Controlling Insect Infestation

The method for preventing and/or controlling insect invasion of the present invention comprises contacting the insect with an effective amount of at least one interfering ribonucleic acid, wherein the interfering ribonucleic acid down-regulates the expression of an essential insect target gene after being ingested by the insect. The essential target gene may be any insect gene involved in regulating an essential biological process required by the insect to initiate or maintain infestation, including but not limited to survival, growth, development, reproduction, and pathogenicity.

The method of the present invention for preventing and/controlling insect invasion in a crop plant field comprises expressing an effective amount of the interfering ribonucleic acid in the plant. In the case where the method is used to control insect invasion, the term "effective amount" refers to an amount or concentration of the interfering ribonucleic acid required to produce a phenotypic effect on the insect so as to reduce the number of insects infesting host organisms and/or to reduce the damage caused by the insect. The phenotypic effect can be the death of the insect and the use of interfering RNA has achieved an insect mortality of at least 20%, 30%, 40%, preferably at least 50%, 60%, 70%, more preferably at least 80% or 90%, as compared with the control insect. The phenotypic effects can also include, but are not limited to, hindering insect growth, stopping feeding, and reducing egg production. Therefore, compared with the control insect, the total number of insects attacking the host organism can be reduced by at least 20%, 30%, 40%, preferably at least 50%, 60%, 70%, more preferably at least 80% or 90%. Optionally, the damage caused by the insect can be reduced by at least 20%, 30%, 40%, preferably at least 50%, 60%, 70%, more preferably at least 80% or 90%, as compared to the control insect. Therefore, the present invention can be used to achieve an insect control of at least 20%, 30%, 40%, preferably at least 50%, 60%, 70%, and more preferably at least 80% or 90%.

The method and composition of the present invention can be used to restrict or eliminate an invasion of a coleopteran pest, preferably *Monolepta hieroglyphica*, within an environment or on a surface where any pest host, pest symbiont or pest exists, by providing one or more compositions containing dsRNA molecules of the present invention in the food of pest. This method is particularly beneficial for preventing insects from attacking plants, and the pests are defined as which digestive system has pH of about 4.5 to about 9.5, about 5 to about 9, about 6 to about 7, and about pH 7.0.

Advantages of the Present Invention

The present invention provides a polynucleotide and method for controlling insect invasion, which have at least the following advantages:

1. The present invention discloses for the first time a plurality of target sequences of the target gene c35112 for controlling a coleopteran insect pest, *Monolepta hieroglyphica*, and verifies that the nucleic acid inhibitor obtained based on these target sequences can be directly used to control the invasion of the coleopteran insect pest.

2. Highly specific to species. The target sequence of the present invention for controlling coleopteran insect pest *Monolepta hieroglyphica* highly specifically acts on *Monolepta hieroglyphica* and species that are closely related to it and have consistent sequences.

3. Avoid resistance. The present invention does not rely on the combination of specific dsRNA and receptor protein in an insect, and can effectively avoid risk such as that the insect generates resistance to Bt toxin protein.

4. The RNAi technology used in the present invention has high efficiency and specificity, and the obtained dsRNA can be directly applied to the field to control the invasion of coleopteran insect pests, which is convenient, low in cost, and has good environmental compatibility.

The technical solutions of the present invention will be further described in detail below through the accompanying drawings and examples.

BRIEF DESCRIPTION OF THE DRAWINGS

FIG. 1 shows an electrophoresis diagram of the expression level of target gene c35112 of the polynucleotide and method for controlling insect invasion of the present invention;

FIG. 2 shows a schematic diagram of the recombinant expression vector DBNR35112C1 vector used in the polynucleotide and method for controlling insect invasion of the present invention.

EXAMPLES

The following specific examples further illustrate the technical solution of the polynucleotide and method of the present invention for controlling insect invasion.

Example 1

Determination of *Monolepta hieroglyphica* Target Sequence

1. Extraction of Total RNA of *Monolepta hieroglyphica*

First-instar worms of *Monolepta hieroglyphica* were used as material, RNA was extracted by the conventional Trizol method, purified by the conventional method, and treated with DNA enzyme to obtain a total RNA sample with a concentration of ≥300 ng/μL, a total amount of ≥6 μg, and an OD 260/280 of 1.8-2.2.

2. Isolation of mRNA and Synthesis of cDNA

Magnetic beads with oligo-dT were used to separate mRNA with polyA from the total RNA sample as prepared above, and then the first strand of cDNA was synthesized with random hexamer and Invitrogen's Superscript II reverse transcriptase kit.

3. Screening of Target Genes

One sample of target gene c35112 of *Monolepta hieroglyphica* was screened out from the larval library analysis of genes with moderate expression levels and possibly involved in important metabolic pathways, its full-length nucleotide sequence was shown in SEQ ID NO:1, and its amino acid sequence was shown in SEQ ID NO: 2.

4. Selection of Target Sequence in Target Gene

Eighteen target sequences with different ORF positions and/or different lengths of target gene c35112 were selected, as shown in Table 1:

TABLE 1

Sequence information of 18 target sequences

| Target sequence | Sequence No. |
|---|---|
| Target sequence 1-r1 | SEQ ID NO: 3 |
| Target sequence 2-r2 | SEQ ID NO: 4 |
| Target sequence 3-r3 | SEQ ID NO: 5 |
| Target sequence 4-r4 | SEQ ID NO: 6 |
| Target sequence 5-r5 | SEQ ID NO: 7 |
| Target sequence 6-r6 | SEQ ID NO: 8 |
| Target sequence 7-r7 | SEQ ID NO: 9 |
| Target sequence 8-r8 | SEQ ID NO: 10 |
| Target sequence 9-r9 | SEQ ID NO: 11 |
| Target sequence 10-r10 | SEQ ID NO: 12 |
| Target sequence 11-r11 | SEQ ID NO: 13 |
| Target sequence 12-r12 | SEQ ID NO: 14 |
| Target sequence 13-r13 | SEQ ID NO: 15 |
| Target sequence 14-r14 | SEQ ID NO: 16 |
| Target sequence 15-r15 | SEQ ID NO: 17 |
| Target sequence 16-r16 | SEQ ID NO: 18 |
| Target sequence 17-r17 | SEQ ID NO: 19 |
| Target sequence 18-r18 | SEQ ID NO: 20 |

Example 2

Production of dsRNA

By referring to the instructions of MEGAscript RNAi Kit of ThermoFisher Company, the dsRNAs of the above 18 target sequences were synthesized, which are r1-dsRNA to r18-dsRNA; and product sizes were detected by agarose electrophoresis with a mass concentration of 1%, and the concentrations of the above r1-dsRNA to r18-dsRNA were determined by using NanoDrop 2000 (Thermo Scientific), respectively.

Example 3

Identification of Control of *Monolepta hieroglyphica* by Feeding dsRNA

The separated and purified r1-dsRNA to r18-dsRNA were mixed separately and added evenly into feed at ratios of 50 μg/g feed and 5 μg/g feed (for feed formula, see: Development of an artificial diet for the western corn rootworm, Entomologia Experimentalis et Applicata 105:1-11, 2002.), and thus c35112-r1-50 to c35112-r18-50 feeds and c35112-r1-5 to c35112-r18-5 feeds were obtained respectively, wherein the control group feed CK was added with irrelevant dsRNA (SEQ ID NO: 29) and other conditions were exactly the same. The newly hatched larvae of *Monolepta hieroglyphica* were fed with the prepared feeds, in which 30 newly hatched larvae with incubation time of no more than 24 hours were placed in each dish, wherein the feeds mixed with dsRNA were changed every two days and fed until the 12th day. Insect mortality was counted every two days from the beginning of feeding. From the beginning of feeding, the expression levels of target genes were measured on Day 0, 4, 8, and 10 by a specific method as follows:

Step 301: the worms that were fed with c35112-r1-50 to c35112-r18-50 feeds and c35112-r1-5 to c35112-r18-5 feeds were collected on Day 0, 4, 8, and 10 respectively, and cryopreservated in liquid nitrogen;

Step 302: the total RNAs of the above-mentioned worms were extracted by using the Trizol method;

Step 303: the total RNAs of the above-mentioned worms were reversely transcribed by using TransGen Biotech ER301-01 to obtain cDNAs;

Step 304: Ubiquitin-C was used as an internal reference gene to perform PCR amplification, and after amplification, 10 uL of the amplified product was subjected to agarose gel electrophoresis with a mass concentration of 1%.

Each treatment in the above experiment was repeated 5 times, and the statistical results were shown in FIG. 1 and Table 2. In Table 2, "-50" in material number means that 50 μg of corresponding dsRNA was contained in per gram of feed, i.e., the aforementioned "50 μg/g feed"; "-5" means that 5 μg of corresponding dsRNA was contained in per gram of feed, i.e., the aforementioned "5 μg/g feed". For example, "r1-dsRNA-50" means that 50 μg of r1-dsRNA was contained in per gram of feed. "DAI" referred to the number of days after feeding.

The results of the target gene expression measurement in FIG. 1 showed that the dsRNA of target sequences r3 and r4 (50 μg/g feed) had a significant inhibitory effect on the expression of the target gene c35112 in *Monolepta hieroglyphica*, the expression of the target gene c35112 had been significantly down-regulated on Day 4 of feeding, and the expression of c35112 was almost undetectable on Day 10.

The dsRNA feeding results in Table 2 showed that the dsRNA of target sequences r1-r18 of the target gene c35112 had obvious lethal effects on *Monolepta hieroglyphica*, and there were almost no surviving larvae in most repeats on Day 12 of feeding.

Example 4

Unexpected Technical Effects of Interfering the Expression of Same Gene in Different Insects Signal recognition particle 54 kDa protein belongs to one of peptide chains in signal recognition particle complex. Its main function is that when the currently secreted protein is exposed from ribosome, the signal recognition particle 54 kDa protein quickly binds to a signal sequence of the presecreted protein, and transfers it to a membrane protein associated with translocation chain. Relevant literature has shown that the interference on the expression of the gene encoding the signal recognition particle 54 kDa protein can have lethal effects on a variety of coleopteran insects; for example, as reported by Julia Ulrich et al. (2015), when the gene encoding the protein in *Tribolium castaneum* was subjected to RNAi interference by injection way (injection of sequence code iB_00404), it was found that the *Tribolium castaneum* was almost all dead within 4 days after injection. Further, as reported by Avet-Rochex et al. (2010), when the gene encoding the protein in *Drosophila* was subjected to RNAi interference by injection (Table 1), the results showed that the *Drosophila* was almost all dead after injection.

TABLE 2

Results of survival rate of dsRNA feeding test of *Monolepta hieroglyphica*

| Material No. | DAI0 | DAI2 | DAI4 | DAI6 | DAI8 | DAI10 | DAI12 |
| --- | --- | --- | --- | --- | --- | --- | --- |
| CK-dsRNA | 100% ± 0% | 100% ± 0% | 96% ± 5% | 96% ± 5% | 92% ± 8% | 87% ± 10% | 85% ± 12% |
| r1-dsRNA-50 | 100% ± 0% | 98% ± 4% | 92% ± 6% | 81% ± 11% | 58% ± 15% | 32% ± 16% | 8% ± 10% |
| r1-dsRNA-5 | 100% ± 0% | 100% ± 0% | 94% ± 6% | 85% ± 9% | 75% ± 14% | 52% ± 10% | 30% ± 16% |
| r2-dsRNA-50 | 100% ± 0% | 100% ± 0% | 90% ± 6% | 78% ± 8% | 47% ± 7% | 27% ± 12% | 12% ± 6% |
| r2-dsRNA-5 | 100% ± 0% | 98% ± 2% | 97% ± 4% | 89% ± 6% | 72% ± 12% | 49% ± 9% | 25% ± 15% |
| r3-dsRNA-50 | 100% ± 0% | 98% ± 4% | 88% ± 7% | 71% ± 10% | 45% ± 9% | 19% ± 15% | 8% ± 5% |
| r3-dsRNA-5 | 100% ± 0% | 100% ± 0% | 93% ± 7% | 89% ± 7% | 77% ± 14% | 56% ± 18% | 28% ± 10% |
| r4-dsRNA-50 | 100% ± 0% | 97% ± 3% | 92% ± 6% | 75% ± 8% | 50% ± 8% | 25% ± 12% | 12% ± 8% |
| r4-dsRNA-5 | 100% ± 0% | 98% ± 3% | 89% ± 8% | 79% ± 10% | 70% ± 10% | 50% ± 10% | 30% ± 15% |
| r5-dsRNA-50 | 100% ± 0% | 100% ± 0% | 86% ± 10% | 68% ± 15% | 35% ± 12% | 10% ± 8% | 5% ± 5% |
| r5-dsRNA-5 | 100% ± 0% | 100% ± 0% | 92% ± 10% | 85% ± 15% | 65% ± 12% | 51% ± 16% | 22% ± 10% |
| r6-dsRNA-50 | 100% ± 0% | 98% ± 4% | 91% ± 7% | 81% ± 9% | 46% ± 12% | 20% ± 8% | 8% ± 6% |
| r6-dsRNA-5 | 100% ± 0% | 100% ± 0% | 95% ± 6% | 86% ± 12% | 70% ± 13% | 55% ± 15% | 28% ± 10% |
| r7-dsRNA-50 | 100% ± 0% | 94% ± 5% | 90% ± 8% | 82% ± 8% | 67% ± 8% | 38% ± 12% | 12% ± 8% |
| r7-dsRNA-5 | 100% ± 0% | 100% ± 0% | 92% ± 6% | 82% ± 12% | 67% ± 14% | 49% ± 11% | 31% ± 14% |
| r8-dsRNA-50 | 100% ± 0% | 100% ± 0% | 93% ± 7% | 77% ± 6% | 55% ± 10% | 28% ± 9% | 16% ± 5% |
| r8-dsRNA-5 | 100% ± 0% | 100% ± 0% | 88% ± 6% | 80% ± 10% | 65% ± 12% | 50% ± 12% | 25% ± 15% |
| r9-dsRNA-50 | 100% ± 0% | 98% ± 2% | 86% ± 8% | 70% ± 10% | 50% ± 10% | 25% ± 10% | 10% ± 10% |
| r9-dsRNA-5 | 100% ± 0% | 100% ± 0% | 95% ± 6% | 82% ± 8% | 59% ± 10% | 41% ± 13% | 27% ± 12% |
| r10-dsRNA-50 | 100% ± 0% | 100% ± 0% | 88% ± 10% | 79% ± 8% | 63% ± 11% | 50% ± 9% | 18% ± 12% |
| r10-dsRNA-5 | 100% ± 0% | 100% ± 0% | 96% ± 5% | 89% ± 6% | 65% ± 10% | 52% ± 12% | 25% ± 10% |
| r11-dsRNA-50 | 100% ± 0% | 95% ± 6% | 86% ± 7% | 67% ± 12% | 50% ± 12% | 32% ± 11% | 10% ± 10% |
| r11-dsRNA-5 | 100% ± 0% | 100% ± 0% | 96% ± 4% | 89% ± 6% | 65% ± 10% | 52% ± 11% | 27% ± 10% |
| r12-dsRNA-50 | 100% ± 0% | 95% ± 7% | 81% ± 7% | 80% ± 9% | 63% ± 14% | 33% ± 7% | 10% ± 5% |
| r12-dsRNA-5 | 100% ± 0% | 99% ± 1% | 83% ± 7% | 74% ± 14% | 44% ± 8% | 41% ± 5% | 17% ± 9% |
| r13-dsRNA-50 | 100% ± 0% | 97% ± 4% | 81% ± 6% | 72% ± 7% | 57% ± 14% | 30% ± 12% | 17% ± 14% |
| r13-dsRNA-5 | 100% ± 0% | 99% ± 2% | 82% ± 7% | 77% ± 10% | 48% ± 6% | 43% ± 11% | 28% ± 10% |
| r14-dsRNA-50 | 100% ± 0% | 98% ± 2% | 94% ± 4% | 73% ± 11% | 62% ± 9% | 31% ± 11% | 17% ± 7% |
| r14-dsRNA-5 | 100% ± 0% | 99% ± 1% | 89% ± 8% | 67% ± 8% | 59% ± 12% | 45% ± 10% | 29% ± 3% |
| r15-dsRNA-50 | 100% ± 0% | 97% ± 2% | 81% ± 6% | 66% ± 12% | 50% ± 12% | 38% ± 12% | 9% ± 12% |
| r15-dsRNA-5 | 100% ± 0% | 99% ± 1% | 82% ± 8% | 74% ± 13% | 48% ± 7% | 46% ± 6% | 21% ± 6% |
| r16-dsRNA-50 | 100% ± 0% | 98% ± 3% | 92% ± 6% | 74% ± 10% | 62% ± 14% | 27% ± 7% | 14% ± 8% |
| r16-dsRNA-5 | 100% ± 0% | 99% ± 1% | 81% ± 4% | 63% ± 14% | 51% ± 12% | 47% ± 10% | 29% ± 6% |
| r17-dsRNA-50 | 100% ± 0% | 97% ± 2% | 90% ± 5% | 85% ± 13% | 64% ± 9% | 25% ± 5% | 18% ± 6% |
| r17-dsRNA-5 | 100% ± 0% | 96% ± 5% | 85% ± 9% | 77% ± 10% | 62% ± 8% | 41% ± 12% | 20% ± 5% |
| r18-dsRNA-50 | 100% ± 0% | 100% ± 0% | 85% ± 7% | 82% ± 6% | 47% ± 13% | 31% ± 13% | 14% ± 6% |
| r18-dsRNA-5 | 100% ± 0% | 97% ± 4% | 85% ± 8% | 83% ± 6% | 43% ± 13% | 36% ± 10% | 28% ± 10% |

Based on the above-mentioned literature reports and high sequence homology, the gene encoding the protein in *Monolepta hieroglyphica* was screened, and the sequence M1 as shown in SEQ ID NO: 30 at the corresponding position was selected according to the sequences injected in *Tribolium castaneum* and *Drosophila*; the sequence M2 as shown in SEQ ID NO:31 at non-corresponding position was also selected. The method of feeding dsRNA (50 μg/g feed ratio) in Example 3 of the present invention was used to identify the control ability to *Monolepta hieroglyphica*. As shown in Table 3, the experimental results showed that neither the sequence M1 at corresponding position nor the sequence M2 at non-corresponding position had obvious lethal effect on *Monolepta hieroglyphica*, which was basically the same as the control. Similar experimental results were confirmed in WO 2018/026770, in which after obtaining the transcription group, RNAi lethal genes of *Nematodes* and *Drosophila* were used for verification, that was, according to the known lethal genes in *Nematodes* and *Drosophila*, the corresponding gene in corn rootworm was subjected to RNAi interference, and basically no obvious lethal effect was observed. In summary, the technical effects of interfering the expression of same gene in different insects are unpredictable, and are not necessarily related to the technical effects of known interference and sequence homology.

plasmids were extracted by alkaline method: the bacterial solution was centrifuged at 12000 rpm for 1 min, the supernatant was discarded, and the precipitated bacterial cells were suspended with 100 μL of ice-precooled Solution I (25 mM Tris-HCl, 10 mM EDTA (ethylenediaminetetraacetic acid), 50 mM glucose, PH8.0); 200 μL of newly prepared Solution II (0.2M NaOH, 1% SDS (sodium dodecyl sulfate)) was added, the tube was inverted 4 times for mixing, and placed on ice for 3-5 min; 150 μL of ice-cooled Solution III (3M potassium acetate, 5M acetic acid) was added, mixed thoroughly immediately, and placed on ice for 5-10 min; after centrifugation for 5 min at a temperature of 4° C. and a rotation speed of 12000 rpm, 2 volumes of absolute ethanol was added to the supernatant, evenly mixed, and stood at room temperature for 5 minutes; centrifugation was carried out for 5 minutes at a temperature of 4° C. and a rotation speed of 12000 rpm, the supernatant was discarded, the precipitate was washed with ethanol with a concentration (V/V) of 70%, and dried in the air; 30 μL of TE (10 mM Tris-HCl, 1 mM EDTA, pH 8.0) containing RNase (20 μg/mL) was added to dissolve the precipitate; digestion of RNA was carried out in a water bath at 37° C. for 30 minutes; stored at −20° C. for later use. The extracted plasmids were sequenced and identified by PCR, and the

TABLE 3

Lethality rate results of dsRNA feeding test of *Monolepta hieroglyphica*

| Material No. | DAI4 | DAI6 | DAI8 | DAI10 | DAI12 | DAI14 |
|---|---|---|---|---|---|---|
| CK-dsRNA | 96% ± 6% | 85% ± 9% | 75% ± 16% | 71% ± 16% | 69% ± 13% | 69% ± 14% |
| M1-dsRNA-50 | 98% ± 3% | 92% ± 6% | 89% ± 7% | 83% ± 9% | 69% ± 15% | 63% ± 18% |
| M2-dsRNA-50 | 91% ± 8% | 88% ± 10% | 84% ± 11% | 76% ± 13% | 69% ± 15% | 67% ± 17% |

Example 5

Construction of Plant Expression Vector

Figure 2:
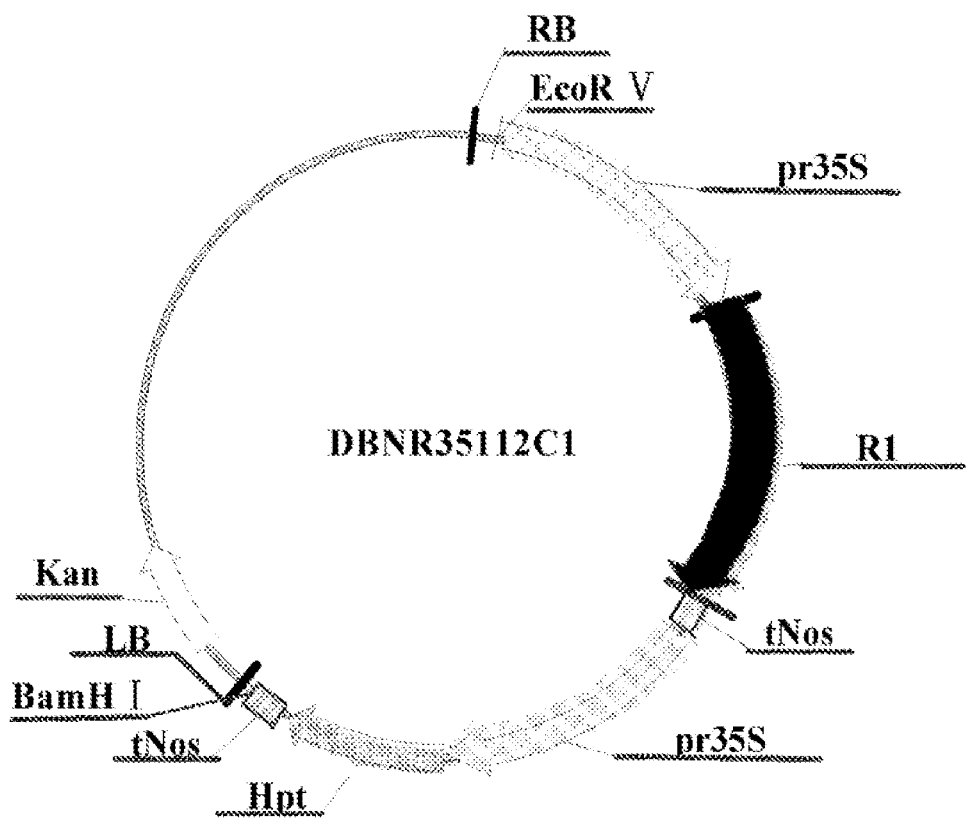

Two expression cassettes were synthesized according to the sequence of p35S-RX-tNos-p35S-Hpt-tNos (X was 1-18), and were ligated to a plant expression vector by using EcoR V and BamH I, and the resultant vectors are named as DBNR35112CX (X was 1-18), wherein the schematic diagram of DBNR35112C1 vector was shown in FIG. 2 (Kan: *kanamycin* gene; RB: right border; pr35S: cauliflower mosaic virus 35S (SEQ ID NO: 21); R1 (SEQ ID NO: 22): the reverse complement sequence of r1 nucleotide sequence (r1 was the target sequence 1 of target gene c35112, SEQ ID NO: 3)+spacer sequence (SEQ ID NO: 23)+r1 nucleotide sequence; tNos: nopaline synthase gene terminator (SEQ ID NO: 24); Hpt: hygromycin phosphotransferase gene (SEQ ID NO: 25); LB: left border).

The recombinant expression vector DBNR35112C1 was transformed into *E. coli* T1 competent cells by the heat shock method, in which the heat shock conditions were: 50 μL of *E. coli* T1 competent cells, 10 μL of plasmid DNA (recombinant expression vector DBNR35112C1), 42° C. water bath for 30 s; 37° C. shaking culture for 1 h (shaking on a shaker at 100 rpm); then cultured at 37° C. for 12 h on a LB solid plate containing 50 mg/L Kanamycin (tryptone 10 g/L, yeast extract 5 g/L, NaCl 10 g/L, agar 15 g/L, adjusted to pH 7.5 with NaOH), the white colonies were picked and cultured overnight at 37° C. in a LB liquid medium (tryptone 10 g/L, yeast extract 5 g/L, NaCl 10 g/L, Kanamycin 50 mg/L, adjusted to pH 7.5 with NaOH). The results showed that the recombinant expression vector DBNR35112C1 was constructed correctly.

The recombinant expression vectors DBNR35112C2 to DBNR35112C18 were constructed according to the above method, and their vector structures were: Kan: *kanamycin* gene; RB: right border; pr35S: cauliflower mosaic virus 35S (SEQ ID NO: 21); RX: rX nucleotide sequence (rX was the target sequence X of target gene c35112, X was 2 to 18)+spacer sequence (SEQ ID NO: 23)+the reverse complement of rX nucleotide sequence; tNos: nopaline synthase gene terminator (SEQ ID NO: 24); Hpt: hygromycin phosphotransferase gene (SEQ ID NO: 25); LB: left border, the recombinant expression vectors DBNR35112C2 to DBNR35112C18 were transformed into *E. coli* T1 competent cells by the heat shock method, and plasmids were extracted by the alkaline method.

Example 6

Transformation of *Agrobacterium* with Recombinant Expression Vector

The correctly constructed recombinant expression vectors DBNR35112C1 to DBNR35112C18 were transformed into *Agrobacterium* LBA4404 (Invitrgen, Chicago, USA, CAT: 18313-015) by the liquid nitrogen method, in which the transformation conditions were: 100 μL of *Agrobacterium* LBA4404, 3 μL of plasmid DNA (recombinant expression vector); placed in liquid nitrogen for 10 minutes, 37° C. warm water bath for 10 minutes; the transformed *Agrobacterium* LBA4404 was inoculated into LB test tube at a temperature of 28° C. and a rotate speed of 200 rpm for 2 h, coated on a LB plate containing 50 mg/L Rifampicin and 100 mg/L Kanamycin until positive monoclone was grown, the monoclone culture was picked and its plasmid was extracted, the recombinant expression vectors DBNR35112C1 to DBNR35112C18 were subjected to enzyme digestion using restriction enzymes EcoR V and BamH I to perform enzyme digestion verification, and the results showed that the structures of the recombinant expression vectors DBNR35112C1 to DBNR35112C18 were completely correct.

Example 7

Production of Transgenic Maize Plants

According to the conventional *Agrobacterium* infection method, immature embryos of aseptically cultured maize variety Z31 (Z31) were co-cultured with the transformed *Agrobacterium* described in Example 6 to transfer the T-DNA (including RX nucleotide sequence, promoter sequence of cauliflower mosaic virus 35S gene, Hpt gene and Nos terminator sequence) of the recombinant expression vectors DBNR35112C1 to DBNR35112C18 as constructed in Example 5 into the maize genome, thereby obtaining maize plants transferred with RX nucleotide sequence (X was 1-18); and wild-type maize plants were used as control at the same time.

For the *Agrobacterium*-mediated maize transformation, briefly, immature embryos were isolated from corn, and the immature embryos were contacted with *Agrobacterium* suspension, wherein *Agrobacterium* was capable of delivering the RX nucleotide sequence to at least one of the immature embryo's cells (Step 1: Infection step). In this step, the immature embryos were preferably immersed in the *Agrobacterium* suspension (OD 660=0.4 to 0.6, infection medium (MS salt 4.3 g/L, MS vitamin, casein 300 mg/L, sucrose 68.5 g/L, glucose 36 g/L, acetosyringone (AS) 40 mg/L, 2,4-dichlorophenoxyacetic acid (2,4-D) 1 mg/L, pH5.3)) to start inoculation. The immature embryos were co-cultured with *Agrobacterium* for a period of time (3 days) (Step 2: Co-cultivation step). Preferably, the immature embryos were placed on a solid medium (MS salt 4.3 g/L, MS vitamins, casein 300 mg/L, sucrose 20 g/L, glucose 10 g/L, acetosyringone (AS) 100 mg/L, 2,4-dichlorophenoxy-acetic acid (2,4-D) 1 mg/L, agar 8 g/L, pH5.8) after the infection step. After this co-cultivation stage, there could be an optional "recovery" step. In the "recovery" step, a recovery medium (MS salt 4.3 g/L, MS vitamins, casein 300 mg/L, sucrose 30 g/L, 2,4-dichlorophenoxyacetic acid (2,4-D) 1 mg/L, plant gel 3 g/L, pH 5.8) contained at least one antibiotic (cephalosporin) that was known to inhibit the growth of *Agrobacterium*, and no selection agent for plant transformant was added (Step 3: Recovery step). Preferably, the immature embryos were cultured on a solid medium containing antibiotic but no selective agent to eliminate *Agrobacterium* and provide a recovery period for the infected cells. Next, the inoculated immature embryos were cultured on a medium containing a selection agent (hygromycin) and the growing transformed callus was selected (Step 4: Selection step). Preferably, the immature embryos were cultured on a solid medium (MS salt 4.3 g/L, MS vitamins, casein 300 mg/L, sucrose 30 g/L, hygromycin 50 mg/L, 2,4-dichlorophenoxyacetic acid (2,4-D) 1 mg/L, plant gel 3 g/L, pH5.8) containing a selection agent, thereby resulting in the selective growth of transformed cells. Then, the callus was regenerated into a plant (Step 5: Regeneration step). Preferably, the callus grown on the medium containing the selection agent was cultured on solid media (MS differentiation medium and MS rooting medium) to regenerate the plant.

The screened resistant callus was transferred to the MS differentiation medium (MS salt 4.3 g/L, MS vitamins, casein 300 mg/L, sucrose 30 g/L, 6-benzylaminopurine 2 mg/L, hygromycin 50 mg/L, plant gel 3 g/L, pH5.8), and cultured at 25° C. for differentiation. The differentiated seedlings were transferred to the MS rooting medium (MS salt 2.15 g/L, MS vitamins, casein 300 mg/L, sucrose 30 g/L, indole-3-acetic acid 1 mg/L, plant gel 3 g/L, PH5.8), cultured at 25° C. to a height of about 10 cm, then moved to a greenhouse and cultivated until fruition. In the greenhouse, the cultivation was performed at 28° C. for 16 hours and then at 20° C. for 8 hours per day.

Example 8

Production of Transgenic Soybean Plants

According to the conventional *Agrobacterium* infection method, the cotyledonary node tissue of sterilely cultured soybean variety Zhonghuang 13 was co-cultured with the transformed *Agrobacterium* described in Example 6 to transfer the T-DNA (including RX nucleotide sequence, cauliflower mosaic virus 35S gene promoter sequence, Hpt gene and Nos terminator sequence) of the recombination expression vectors DBNR35112C1 to DBNR35112C18 into the soybean genome, thereby obtaining soybean plants transferred with RX nucleotide sequence (X is 1-18); and wild-type soybean plants were used as control at the same time.

For the *Agrobacterium*-mediated soybean transformation, briefly, mature soybean seeds were germinated in soybean germination medium (B5 salt 3.1 g/L, B5 vitamin, sucrose 20 g/L, agar 8 g/L, pH5.6), the seeds were inoculated on germination medium and cultivated under the following conditions: temperature was 25±1° C.; photoperiod (light/dark) was 16/8 h. After 4 to 6 days of germination, aseptic soybean seedlings with enlarged cotyledon nodes in bright green were selected, the hypocotyls 3-4 mm below the cotyledon nodes were cut off, the cotyledons were cut longitudinally, then apical buds, lateral buds and seed roots were removed. Scalpel back was used to wound the cotyledon node, and the wounded cotyledon node tissue contacted with *Agrobacterium* suspension, wherein the *Agrobacterium* could transfer the RX nucleotide sequence to the wounded cotyledon node tissue (Step 1: Infection step). In this step, the cotyledon node tissue was preferably immersed in the *Agrobacterium* suspension (OD 660=0.5 to 0.8, infection medium (MS salt 2.15 g/L, B5 vitamin, sucrose 20 g/L, glucose 10 g/L, acetylsyringone (AS) 40 mg/L, 2-morpholineethanesulfonic acid (MES) 4 g/L, zeatin (ZT) 2 mg/L, pH5.3) to start inoculation. The cotyledon node tissue and *Agrobacterium* were co-cultured for a certain period (3 days) (Step 2: Co-cultivation step). Preferably, after the infection step, the cotyledon node tissue was placed in a solid medium (MS salt 4.3 g/L, B5 vitamin, sucrose 20 g/L, glucose 10 g/L, 2-morpholineethanesulfonic acid (MES) 4 g/L, zeatin 2 mg/L, agar 8 g/L, pH 5.6). After this co-cultivation stage, there could be an optional "recovery" step. In the "recovery" step, recovery medium (B5 salt 3.1 g/L, B5 vitamins, 2-morpholineethanesulfonic acid (MES) 1 g/L, sucrose 30 g/L, zeatin (ZT) 2 mg/L, agar 8 g/L, cephalosporin 150 mg/L, glutamic acid 100 mg/L, aspartic acid 100 mg/L, pH 5.6) contained at least one antibiotic (cephalosporin) that is known to inhibit the growth of *Agrobacterium*, and no selective agent for plant transformant was added (Step 3: Recovery step). Preferably, the regenerated tissue mass of the cotyledon node was cultured on a solid medium with antibiotic but no selective agent to eliminate *Agrobacterium* and provide a recovery period for the infected cells. Next, the regenerated tissue mass of the cotyledon node was cultured on a medium containing a selection agent (hygromycin) and the growing transformed callus was selected (Step 4: Selection step). Preferably, the regenerated tissue mass of the cotyledon node was cultured on a screening solid medium with selective agent (B5 salt 3.1 g/L, B5 vitamin, 2-morpholineethanesulfonic acid (MES) 1 g/L, sucrose 30 g/L, 6-benzylaminopurine (6-BAP) 1 mg/L, agar 8 g/L, cephalosporin 150 mg/L, glutamic acid 100 mg/L, aspartic acid 100 mg/L, hygromycin 50 mg/L, pH 5.6), resulting in selective growth of the transformed cell. Then, the transformed cell was regenerate to a plant (Step 5: Regeneration step); preferably, the regenerated tissue mass of the cotyledon node grown on the medium containing the selection agent was cultured in solid media (B5 differentiation medium and B5 rooting medium) to regenerate the plant.

The screened resistant tissue mass was transferred to the B5 differentiation medium (B5 salt 3.1 g/L, B5 vitamins, 2-morpholineethanesulfonic acid (MES) 1 g/L, sucrose 30 g/L, zeatin (ZT) 1 mg/L, agar 8 g/L, cephalosporin 150 mg/L, glutamic acid 50 mg/L, aspartic acid 50 mg/L, gibberellin 1 mg/L, auxin 1 mg/L, hygromycin 50 mg/L, PH5.6), cultured at 25° C. for differentiation. The differentiated seedlings were transferred to the B5 rooting medium (B5 salt 3.1 g/L, B5 vitamins, 2-morpholineethanesulfonic acid (MES) 1 g/L, sucrose 30 g/L, agar 8 g/L, cephalosporin 150 mg/L, indole-3-butyric acid (IBA) 1 mg/L), cultured in rooting medium at 25° C. to a height of about 10 cm, moved to a greenhouse and cultivated until fruition. In the greenhouse, cultivation was carried out at 26° C. for 16 hours and then at 20° C. for 8 hours per day.

Example 9

Verification of Transgenic Maize and Soybean Plants by TaqMan

About 100 mg of the leaves of the maize plants transferred with RX nucleotide sequences (X was 1 was 18) as samples were separately taken, and their genomic DNAs were extracted with DNeasy Plant Maxi Kit of Qiagen, respectively, and the copy numbers of the RX nucleotide sequences were determined by detecting the copy number of Hpt gene by Taqman probe fluorescence quantitative PCR method. At the same time, wild-type maize plants were used as control, and subjected to the detection and analysis according to the above methods. The experiment was repeated 3 times and the average value was taken.

The specific method for detecting the copy number of Hpt gene was as follows:

Step 901: 100 mg of each of the leaves of the maize plant transferred with RX nucleotide sequence and the wild-type maize plant was separately taken, and ground into a homogenate with liquid nitrogen in a mortar respectively, and 3 repeats were taken for each sample;

Step 902: the genomic DNA of the above-mentioned sample was extracted by using DNeasy Plant Mini Kit of Qiagen, and the product manual thereof was referred to for the specific method;

Step 903: NanoDrop 2000 (Thermo Scientific) was used to measure the genomic DNA concentration of the above sample;

Step 904: the genomic DNA concentration of the above sample was adjusted to the same concentration value, and the range of the concentration value was 80 to 100 ng/μL;

Step 905: the Taqman probe fluorescence quantitative PCR method was used to identify the copy number of the sample, the identified sample with known copy number was used as a standard product, and the wild-type maize plant sample was used as control, 3 repeats were taken for each sample, and the average value thereof was taken; the sequences of the primers and probes for fluorescence quantitative PCR were:

the following primers and probes were used to detect the Hpt nucleotide sequence:

Primer 1: cagggtgtcacgttgcaaga as shown in SEQ ID NO: 26 in the sequence listing;

Primer 2: ccgctcgtctggctaagatc as shown in SEQ ID NO: 27 in the sequence listing;

Probe 1: tgcctgaaaccgaactgcccgctg as shown in SEQ ID NO: 28 in the sequence listing;

the PCR reaction system was:

| | |
|---|---|
| JumpStart ™ Taq ReadyMix ™ (Sigma) | 10 μL |
| 50× primer/probe mixture | 1 μL |
| Genomic DNA | 3 μL |
| Water (ddH₂O) | 6 μL | the 50× primer/probe mixture contained 45 μL of each primer at a concentration of 1 mM, 50 μL of probe at a concentration of 100 μM, and 860 μL of 1× TE buffer, and was stored in a centrifuge tube at 4° C.

The PCR reaction conditions were:

| Step | Temperature | Time |
|---|---|---|
| 911 | 95° C. | 5 min |
| 912 | 95° C. | 30 s |
| 913 | 60° C. | 1 min |
| 914 | returned to step 712, repeated for 40 cycles | |

The data was analyzed using SDS2.3 software (Applied Biosystems).

By analyzing the experimental results of the copy number of the Hpt gene, it was confirmed that the RX nucleotide sequences had been integrated into the chromosome of the tested maize plants, respectively, and single-copy transgenic maize plants had been obtained from the maize plants transferred with the RX nucleotide sequences (X was 1-18).

According to the above method of using TaqMan to verify transgenic maize plants, the transgenic soybean plants were detected and analyzed. By analyzing the experimental results of the copy number of the Hpt gene, it was confirmed that the RX nucleotide sequences had been integrated into the chromosome of the tested soybean plants, and single-copy transgenic soybean plant had been obtained from the soybean plants transferred with the RX nucleotide sequences (X was 1-18).

Example 10

Identification of Insecticidal Effects of Transgenic Maize on *Monolepta hieroglyphica*

The maize plants transformed with the RX nucleotide sequences (X was 1-18) were tested for insect resistance effect on *Monolepta hieroglyphica*.

Step 1001: 10 plants of each of single-copy DBNR35112C1 to DBNR35112C18 maize transformation events (RX-M) identified as positive by taqman and 3 plants of maize transformation event (NGM1) identified as negative by taqman were selected respectively; the wild-type maize plant was used as control (CK1) at the same time; and they were planted in a greenhouse to three-leaf stage;

Step 1002: the materials described in Step 1001 were taken, the third tender leaf from each seedling was taken, cut into 1×2 cm to remove leave blade of main vein, and the leave blade was tiled in a petri dish covered with moisturizing filter paper;

Step 1003: 10 newly hatched larvae of *Monolepta hieroglyphica* with an incubation time of no more than 24 hours were placed in each petri dish, and the lid of petri dish was closed, the petri dish was placed into a bioassay box with moisturizing gauze at bottom, and the bioassay box was placed in a bioassay chamber with a temperature of 24±2° C., a D/L of 24/0, and a humidity of 70-80% (i.e., "bioassay");

Step 1004: considering that the newly hatched larvae of *Monolepta hieroglyphica* were weak and prone to mechanical damage, the petri dish was kept as still as possible on the day of inoculation and the first day after inoculation;

Step 1005: from Day 2 of inoculation, the number of surviving *Monolepta hieroglyphica* was counted from outside the petri dish every day until the end of Day 16; the surviving *Monolepta hieroglyphica* in the petri dish were transferred to a petri dish with fresh leaves every 2 days, and the experimental results were shown in Table 4.

Example 11

Identification of Insecticidal Effects of Transgenic Soybeans on *Monolepta hieroglyphica*

The soybean plants transformed with the RX nucleotide sequences (X was 1 to 18) were tested for insect resistance to *Monolepta hieroglyphica*.

Step 1101: 10 plants of each of single-copy DBNR35112C1 to DBNR35112C18 soybean transformation events (RX-S) identified as positive by taqman and 3 plants of soybean transformation event (NGM2) identified as negative by taqman were selected respectively; the wild-type soybean plant was used as control (CK2) at the same time; they were planted in a greenhouse to three true leaves were grown;

Step 1102: the materials described in Step 1101 were taken, a piece of true leaf of about 2×2 cm was taken from each seedling, and tiled in a petri dish covered with moisturizing filter paper;

Step 1103: 15 newly hatched larvae of *Monolepta hieroglyphica* with an incubation time of no more than 24 hours were placed in each dish, and the lid of petri dish was closed, the petri dish was placed into a bioassay box with moisturizing gauze at bottom, and the bioassay box was placed in a bioassay chamber with a temperature of 24±2° C., a D/L of 24/0, and a humidity of 70-80%;

Step 1104: considering that the newly hatched larvae of *Monolepta hieroglyphica* were weak and prone to mechanical damage, the petri dish was kept as still as possible on the day of inoculation and the first day after inoculation;

TABLE 4

Experimental results of feeding *Monolepta hieroglyphica* with leaves of maize transformation events

| Material No. | Survival rate of *Monolepta hieroglyphica* every 2 days after bioassay | | | | | | | |
|---|---|---|---|---|---|---|---|---|
| | DAI2 | DAI4 | DAI6 | DAI8 | DAI10 | DAI12 | DAI14 | DAI16 |
| CK1 | 100% ± 0% | 91% ± 4% | 92% ± 6% | 89% ± 5% | 82% ± 10% | 78% ± 9% | 76% ± 12% | 72% ± 10% |
| NGM1 | 100% ± 0% | 96% ± 0% | 92% ± 4% | 88% ± 4% | 83% ± 13% | 80% ± 10% | 78% ± 11% | 75% ± 9% |
| R1-M | 100% ± 0% | 97% ± 4% | 98% ± 2% | 78% ± 8% | 64% ± 12% | 41% ± 11% | 32% ± 12% | 20% ± 11% |
| R2-M | 100% ± 0% | 96% ± 5% | 92% ± 4% | 84% ± 6% | 66% ± 11% | 42% ± 10% | 33% ± 9% | 43% ± 10% |
| R3-M | 100% ± 0% | 97% ± 4% | 87% ± 6% | 75% ± 8% | 63% ± 14% | 47% ± 14% | 33% ± 8% | 21% ± 12% |
| R4-M | 100% ± 0% | 93% ± 4% | 87% ± 8% | 81% ± 6% | 65% ± 13% | 66% ± 12% | 41% ± 10% | 28% ± 10% |
| R5-M | 100% ± 0% | 95% ± 3% | 88% ± 8% | 76% ± 12% | 62% ± 10% | 45% ± 10% | 31% ± 9% | 25% ± 10% |
| R6-M | 100% ± 0% | 99% ± 1% | 96% ± 3% | 87% ± 8% | 65% ± 15% | 69% ± 9% | 52% ± 10% | 21% ± 11% |
| R7-M | 100% ± 0% | 91% ± 5% | 93% ± 4% | 77% ± 10% | 62% ± 14% | 66% ± 12% | 54% ± 10% | 22% ± 13% |
| R8-M | 100% ± 0% | 99% ± 2% | 92% ± 5% | 77% ± 11% | 72% ± 10% | 49% ± 10% | 36% ± 9% | 27% ± 10% |
| R9-M | 100% ± 0% | 100% ± 0% | 98% ± 2% | 88% ± 9% | 72% ± 13% | 53% ± 11% | 30% ± 10% | 26% ± 9% |
| R10-M | 100% ± 0% | 99% ± 2% | 99% ± 1% | 85% ± 10% | 67% ± 14% | 62% ± 12% | 52% ± 10% | 26% ± 10% |
| R11-M | 100% ± 0% | 98% ± 2% | 92% ± 5% | 84% ± 9% | 73% ± 12% | 67% ± 10% | 38% ± 12% | 33% ± 15% |
| R12-M | 100% ± 0% | 94% ± 4% | 90% ± 7% | 86% ± 10% | 68% ± 10% | 49% ± 9% | 44% ± 9% | 33% ± 10% |
| R13-M | 100% ± 0% | 100% ± 0% | 94% ± 4% | 75% ± 10% | 60% ± 12% | 57% ± 10% | 39% ± 10% | 27% ± 10% |
| R14-M | 100% ± 0% | 97% ± 2% | 87% ± 6% | 86% ± 12% | 61% ± 15% | 52% ± 12% | 36% ± 12% | 18% ± 12% |
| R15-M | 100% ± 0% | 92% ± 5% | 90% ± 6% | 77% ± 12% | 69% ± 12% | 59% ± 10% | 45% ± 9% | 25% ± 10% |
| R16-M | 100% ± 0% | 96% ± 2% | 89% ± 5% | 77% ± 11% | 75% ± 14% | 66% ± 11% | 51% ± 9% | 26% ± 9% |
| R17-M | 100% ± 0% | 92% ± 3% | 91% ± 4% | 89% ± 9% | 71% ± 13% | 64% ± 12% | 37% ±10% | 21% ± 10% |
| R18-M | 100% ± 0% | 93% ± 4% | 90% ± 5% | 84% ± 10% | 75% ± 10% | 41% ± 10% | 58% ± 12% | 24% ± 9% |

The experimental results in Table 4 showed that the maize plants transformed with the RX nucleotide sequences (X was 1 to 18) had good inhibitory effect on *Monolepta hieroglyphica*, and the survival rate of *Monolepta hieroglyphica* on Day 16 (survival rate=number of surviving insects/number of tested insects) was about 30%.

Step 1105: from Day 2 of inoculation, the number of surviving *Monolepta hieroglyphica* was counted from outside the petri dish every day until the end of Day 16; the surviving *Monolepta hieroglyphica* in the petri dish were transferred to a petri dish with fresh true leaves every 2 days, and the experimental results were shown in Table 5.

TABLE 5

Experimental results of feeding Monolepta hieroglyphica with leaves of soybean transformation events

| Material | Survival rate of Monolepta hieroglyphica every 2 days after bioassay | | | | | | | |
|---|---|---|---|---|---|---|---|---|
| No. | DAI2 | DAI4 | DAI6 | DAI8 | DAI10 | DAI12 | DAI14 | DAI16 |
| CK2 | 100% ± 0% | 91% ± 4% | 91% ± 5% | 88% ± 5% | 82% ± 10% | 78% ± 9% | 78% ± 12% | 75% ± 8% |
| NGM2 | 100% ± 0% | 96% ± 0% | 92% ± 4% | 88% ± 4% | 85% ± 10% | 81% ± 9% | 75% ± 10% | 73% ± 8% |
| R1-S | 100% ± 0% | 98% ± 3% | 87% ± 5% | 83% ± 9% | 74% ± 6% | 65% ± 8% | 43% ± 10% | 25% ± 6% |
| R2-S | 100% ± 0% | 99% ± 1% | 87% ± 4% | 79% ± 8% | 69% ± 8% | 56% ± 10% | 44% ± 9% | 18% ± 11% |
| R3-S | 100% ± 0% | 96% ± 5% | 87% ± 6% | 81% ± 10% | 70% ± 16% | 62% ± 10% | 47% ± 12% | 23% ± 12% |
| R4-S | 100% ± 0% | 97% ± 3% | 86% ± 8% | 79% ± 9% | 74% ± 12% | 56% ± 9% | 44% ± 8% | 20% ± 14% |
| R5-S | 100% ± 0% | 100% ± 0% | 87% ± 9% | 82% ± 8% | 67% ± 9% | 50% ± 10% | 41% ± 10% | 24% ± 9% |
| R6-S | 100% ± 0% | 99% ± 2% | 93% ± 7% | 83% ± 8% | 71% ± 9% | 60% ± 12% | 38% ± 6% | 21% ± 12% |
| R7-S | 100% ± 0% | 99% ± 2% | 89% ± 8% | 85% ± 6% | 79% ± 10% | 64% ± 8% | 39% ± 10% | 27% ± 9% |
| R8-S | 100% ± 0% | 96% ± 3% | 90% ± 6% | 83% ± 8% | 79% ± 10% | 54% ± 8% | 46% ± 9% | 25% ± 12% |
| R9-S | 100% ± 0% | 96% ± 4% | 87% ± 8% | 80% ± 9% | 76% ± 8% | 58% ± 6% | 54% ± 6% | 20% ± 18% |
| R10-S | 100% ± 0% | 96% ± 3% | 88% ± 9% | 85% ± 11% | 78% ± 6% | 65% ± 10% | 30% ± 12% | 27% ± 12% |
| R11-S | 100% ± 0% | 96% ± 2% | 89% ± 8% | 84% ± 12% | 79% ± 5% | 50% ± 9% | 49% ± 8% | 21% ± 10% |
| R12-S | 100% ± 0% | 97% ± 1% | 85% ± 10% | 78% ± 9% | 65% ± 9% | 59% ± 11% | 42% ± 10% | 27% ± 10% |
| R13-S | 100% ± 0% | 95% ± 3% | 92% ± 8% | 83% ± 8% | 74% ± 10% | 63% ± 10% | 42% ± 11% | 27% ± 14% |
| R14-S | 100% ± 0% | 98% ± 2% | 90% ± 8% | 84% ± 7% | 66% ± 9% | 52% ± 8% | 38% ± 12% | 20% ± 9% |
| R15-S | 100% ± 0% | 96% ± 3% | 94% ± 6% | 78% ± 6% | 69% ± 10% | 57% ± 9% | 44% ± 12% | 16% ± 11% |
| R16-S | 100% ± 0% | 95% ± 4% | 86% ± 10% | 87% ± 7% | 80% ± 12% | 59% ± 10% | 40% ± 9% | 22% ± 15% |
| R17-S | 100% ± 0% | 99% ± 1% | 94% ± 9% | 83% ± 6% | 75% ± 10% | 66% ± 9% | 41% ± 13% | 20% ± 13% |
| R18-S | 100% ± 0% | 97% ± 3% | 92% ± 8% | 89% ± 4% | 82% ± 9% | 52% ± 7% | 44% ± 8% | 34% ± 12% |

The experimental results in Table 5 showed that the soybean plants transformed with the RX nucleotide sequences (X was 1 to 18) had good inhibitory effect on Monolepta hieroglyphica, and the survival rate of Monolepta hieroglyphica on Day 16 (survival rate=number of surviving insects/number of tested insects) was 35% or less.

Example 12

Composition

The pesticidally acceptable carrier formula of dsRNA (1 L system): 50 mM NaHPO$_4$ (pH7.0), 10 mM β-mercaptoethanol, 10 mM EDTA, 0.1% (mass fraction) sodium cetyl sulfonate, 0.1% (mass fraction) polyethylene glycol octyl phenyl ether, added with H$_2$O to make up to 1 L.

The above formula was a buffer formula, and it was only needed to directly add any purified dsRNA into the buffer, as long as the final concentration met the requirement, such as 50 mg/L. It could also be prepared as a concentrated formulation as needed.

In summary, the present invention discloses for the first time the target gene c35112 and its target sequence for the control of coleopteran insect pest Monolepta hieroglyphica, and the transgenic plants (maize and soybean) are obtained by RNAi technology; the transgenic plants are introduced with dsRNA sequence formed by the target sequence and can control the invasion of Monolepta hieroglyphica, they are efficient and specific and can avoid risk such as that Monolepta hieroglyphica generates resistance to Bt toxin proteins. At the same time, they have good environmental compatibility, convenience and low cost.

Finally, it should be noted that the above examples are only used to illustrate the technical solutions of the present invention and not to limit them. Although the present invention has been described in detail with reference to preferred examples, those of ordinary skill in the art should understand that the technical solutions of the present invention can be subjected to modifications or equivalent replacements without departing from the spirit and scope of the technical solutions of the present invention.

What is claimed is:

1. An isolated nucleic acid for controlling coleopteran insect pest invasion, wherein the isolated nucleic acid comprises a polynucleotide operably linked to a heterologous promoter, wherein the polynucleotide comprises a nucleotide sequence that is at least 99% identical to a fragment of SEQ ID NO: 1 that is at least 139 nucleotides in length and a sequence complementary to the nucleotide sequence, wherein when a coleopteran insect pest ingests a double-stranded RNA encoded by said polynucleotide, the growth of the coleopteran insect pest is inhibited, and wherein the coleopteran insect pest is *Monolepta hieroglyphica*.

2. The isolated nucleic acid according to claim 1, wherein the isolated nucleic acid further comprises a spacer sequence.

3. The isolated nucleic acid according to claim 2, wherein the spacer sequence is SEQ ID NO: 23.

4. A recombinant vector, comprising the isolated nucleic acid according to claim 1.

5. An interfering ribonucleic acid encoded by the polynucleotide according to claim 1.

6. The interfering ribonucleic acid according to claim 5, wherein the interfering ribonucleic acid comprises at least two silencing elements, and each of the silencing elements comprises a nucleotide sequence that is at least partially complementary to a target sequence in a target gene in the insect pest.

7. The interfering ribonucleic acid according to claim 6, wherein each of the silencing elements comprises a different nucleotide sequence that is complementary to a different target sequence.

8. The interfering ribonucleic acid according to claim 7, wherein the different target sequence is derived solely from the target gene.

9. The interfering ribonucleic acid according to claim 7, wherein the different target sequence is derived from a further target gene different from a target gene comprising SEQ ID NO: 1.

10. The interfering ribonucleic acid according to claim 9, wherein the interfering ribonucleic acid further comprises a spacer sequence.

11. The interfering ribonucleic acid according to claim 10, wherein the spacer sequence is SEQ ID NO:23.

12. A composition for controlling coleopteran insect pest invasion, the composition comprising:
    (a) at least one interfering ribonucleic acid encoded by the polynucleotide according to claim 1 or
    (b) a host cell comprising the nucleic acid according to claim 1, and at least one suitable carrier, excipient or diluent, wherein the coleopteran insect pest is *Monolepta hieroglyphica*.

13. The composition for controlling coleopteran insect pest invasion according to claim 12, wherein the host cell is a bacterial cell.

14. The composition for controlling coleopteran insect pest invasion according to claim 12, wherein the composition is solid, liquid or gel.

15. The composition for controlling coleopteran insect pest invasion according to claim 14, wherein the composition is an insecticidal spray.

16. The composition for controlling coleopteran insect pest invasion according to claim 12, wherein the composition further comprises at least one insecticide, and the insecticide is a chemical insecticide, potato tuber specific protein, *Bacillus thuringiensis* insecticidal protein, *Xenorhabdus ehlersii* insecticidal protein, *Photorhabdus luminescens* insecticidal protein, *Bacillus laterosporus* insecticidal protein or *Bacillus sphaericus* insecticidal protein.

17. A method for controlling coleopteran insect pest invasion, comprising contacting a coleopteran insect pest with an effective amount of at least one interfering ribonucleic acid according to claim 5, wherein the coleopteran insect pest is *Monolepta hieroglyphica*.

18. A method for improving resistance to coleopteran insect pest in a plant, producing a plant for controlling coleopteran insect pest, or protecting a plant from damage caused by coleopteran insect pest, comprising introducing one of the following into the plant:
- the nucleic acid according to claim 1;
- a recombinant vector comprising the nucleic acid according to claim 1, or
- an interfering ribonucleic acid encoded by the polynucleotide according to claim 1;

wherein the interfering ribonucleic acid comprises at least one silencing element, wherein the silencing element is a double-stranded RNA region comprising complementary strands which have been annealed, and one strand of which comprises a nucleotide sequence at least partially complementary to a target sequence within a target gene in the coleopteran insect pest, wherein the coleopteran insect pest is *Monolepta hieroglyphica*.

19. The isolated nucleic acid according to claim 1, wherein the nucleotide sequence comprises SEQ ID NO: 1.

20. The isolated nucleic acid according to claim 1, wherein the polynucleotide sequence comprises one of the polynucleotide sequences selected from the full length sequences of SEQ ID NO: 1 SEQ ID NO: 3 to 20.

21. The interfering ribonucleic acid according to claim 9, wherein the further target gene different from the target gene is derived from the same coleopteran insect pest.

22. The interfering ribonucleic acid according to claim 9, wherein the further target gene different from the target gene is derived from the a different coleopteran insect pest.

* * * * *

SEQUENCE LISTING

<160> NUMBER OF SEQ ID NOS: 31

<210> SEQ ID NO 1
<211> LENGTH: 2994
<212> TYPE: DNA
<213> ORGANISM: Monolepta hieroglyphica

<400> SEQUENCE: 1

```
caagagccac gtataaaaca aggttacaga ttttggacaa ctcaaaaaat agtgatgtgt      60
ttataattcg tgtcatttca agaagattaa acaaaaattg ctggataata acccttaaaa     120
atgccacttc gattagatat aaagagaagg ctaacagccc gttcagaccg ggttaaatgc     180
gtggatcttc atccgacaga accctggatg ttatgttctc tgtacagtgg aaatataaat     240
gtctggaata ctgaaaatca acaactggtt aaaactttg aagtatgtga catacctgtt      300
agagctgcaa agtttgtacc tagaaagaac tggattgtca gtggttcaga tgatatgcag     360
```

-continued

```
ataagagttt ttaactacaa tacactagac agggtacact ctttcgaagc ccattcagat    420
tatgtgaggt ctattgtggt acatccaaca caaccatata ttttaacaag tagtgatgat    480
atgcttatca aactgtggaa ctgggaaaag gcatgggctt gtcagcaagt gtttgaagga    540
catactcatt atattatgca aattgcaata aatcccaaag acaacaatac atttgccagt    600
gcatctctag atagaacatt aaaagtgtgg cagctaggtg catcaacagc taacttcact    660
cttgaagggc atgagaaagg tgtcaattgt gtagactact accacggagg tgataaaccc    720
tatataatat caggagccga tgataggttg gtcaaaatct gggattacca aaataaaaca    780
tgtgttcaaa ccttagaagg acatggtcaa aatgttactg ctgtcttttt ccatccagaa    840
cttccagttg ctcttacggg aagtgaagat ggtacagtga aatatggca tgcaaatacc     900 catcgactgg aaagtacctt aaattatgga tttgaaaggg tttggaccat tgttgctta    960 aaaggaagta ataatgtggc attgggttat gacgagggta gtattcttgt taaagttggt   1020
agagaagaac cagctgttag tatggatgcc agtggtggta aaattatttg gctaggcac    1080 tcagaactcc aacaagccaa tcttaaggca ttgcctgaag gtgctgaaat aaaagatgga   1140
gaacgacttc cagtatctgt aaaggatatg ggtgcctgtg aaatctatcc tcaaaccatt   1200
caacacaatc ccaatggtcg ttttgtagtt gtgtgtggag atggtgaata tataatttac   1260
actgccatgg ccttacgtaa caaagcattt ggaagtgcac aagaattcgt ttgggcccaa   1320
gattctagtg aatatgctat tagagaatca ggatctacta aaggatatt taaaaatttc    1380 aaagaaaaga aaaatttcaa gtctgatttt ggagctgaag gtatatatgg gggttacctt   1440
ttgggagtca atctgtttc tgggttaact ttctatgatt gggatacact tgatttggtt    1500
agaaggattg agatacaacc aaaagctgtc tattggtcag atagtggaaa gttggtatgt   1560
ttggccaccg aagatagtta ttttatttta tcatatgatg ctgatgaagt gcaaaaagct   1620
aaagataata atcaagttgc tgacgatggt gtggaatctg cattcaacct tttaggagaa   1680
atcaacgaat ctgttagaac aggcctatgg gtaggtgatt gtttcatcta cacaaatgct   1740
gtgaatcgta tcaattactt tgtaggaggt gaactagtaa ctatcgcaca cttggatcgt   1800
ccattgtacg tcttgggtta tgtgcccaaa gacgatcgtt tgtatctagt agataaagag   1860
ttacgagttg tcagctacca attgcttctt tcagtactcg aatatcagac agctgttatg   1920
aggagggact tcccaacagc agatagagta ctaccgtcta tacctaaaga gcacagaaca   1980
agggtagcac atttcttaga aaagcaaggt tttaaacaac aagctttagc tgtaagttcc   2040
gatcccgaac atagattcga actcgctgtg gcattagaag acctgaatac agctaaaatt   2100
ctagcacaag aggctaacaa tccacaaaag tggagccaat tagctgatct agctgctggc   2160
acaaataatg tagaactagc aaaagaatgc atgcagaaag cccaagattt tggtggatta   2220
ttacttctag ccactagttc gggagatgaa tcattagtcc gtacattagg tgaaacaaca   2280
caagctgagg gcaaacataa tttagccttc ctttctcatt tcttggtagg agatttagac   2340
aagtgtctag atattttagt aagtacagga aggttgccag aagctgcgtt tttcgccaga   2400
tcttatcttc ccgataaaat ttctgaagtt gtagaattgt ggaggacaca attatcaact   2460
ataaatcaaa aagccggaca aagtttagcc gatcctaaaa attatgaaaa tctatttccc   2520
ggtcttcaac aagcattgtc ggcacagaaa ttttggaac agaacaaaca gttgccacct    2580
gcatttatgg ctccttctat tgttcccaac caagatagaa atgttatagc cgaagcggag   2640
gcacagttaa agaatagtgg aacttcatca aatttgttca gtgccccacc ttcagcagaa   2700
```

-continued

```
acttctagga atgttataga atcagtacca caaaataagc cctcagaaga tttatcaaac    2760
agggtgttat tagatcaaga tgatgatgat gacatagact tggatttgga tggcgtcaat    2820
attgacgata acatcgatac aactgatatc aacttggatg atgatttgct gagtgattaa    2880
aaataacttt ttttactatt ttagtattaa tctgtatatt attcattcct aatttttaag    2940
aaaataaatt atgtaagata atgttttatt aactaaaata tggtaattca aaac          2994
```

<210> SEQ ID NO 2
<211> LENGTH: 919
<212> TYPE: PRT
<213> ORGANISM: Monolepta hieroglyphica

<400> SEQUENCE: 2

```
Met Pro Leu Arg Leu Asp Ile Lys Arg Arg Leu Thr Ala Arg Ser Asp
1               5                   10                  15

Arg Val Lys Cys Val Asp Leu His Pro Thr Glu Pro Trp Met Leu Cys
                20                  25                  30

Ser Leu Tyr Ser Gly Asn Ile Asn Val Trp Asn Thr Glu Asn Gln Gln
            35                  40                  45

Leu Val Lys Thr Phe Glu Val Cys Asp Ile Pro Val Arg Ala Ala Lys
        50                  55                  60

Phe Val Pro Arg Lys Asn Trp Ile Val Ser Gly Ser Asp Asp Met Gln
65                  70                  75                  80

Ile Arg Val Phe Asn Tyr Asn Thr Leu Asp Arg Val His Ser Phe Glu
                85                  90                  95

Ala His Ser Asp Tyr Val Arg Ser Ile Val Val His Pro Thr Gln Pro
            100                 105                 110

Tyr Ile Leu Thr Ser Ser Asp Asp Met Leu Ile Lys Leu Trp Asn Trp
        115                 120                 125

Glu Lys Ala Trp Ala Cys Gln Gln Val Phe Glu Gly His Thr His Tyr
130                 135                 140

Ile Met Gln Ile Ala Ile Asn Pro Lys Asp Asn Asn Thr Phe Ala Ser
145                 150                 155                 160

Ala Ser Leu Asp Arg Thr Leu Lys Val Trp Gln Leu Gly Ala Ser Thr
                165                 170                 175

Ala Asn Phe Thr Leu Glu Gly His Glu Lys Gly Val Asn Cys Val Asp
            180                 185                 190

Tyr Tyr His Gly Gly Asp Lys Pro Tyr Ile Ile Ser Gly Ala Asp Asp
        195                 200                 205

Arg Leu Val Lys Ile Trp Asp Tyr Gln Asn Lys Thr Cys Val Gln Thr
210                 215                 220

Leu Glu Gly His Gly Gln Asn Val Thr Ala Val Phe Phe His Pro Glu
225                 230                 235                 240

Leu Pro Val Ala Leu Thr Gly Ser Glu Asp Gly Thr Val Arg Ile Trp
                245                 250                 255

His Ala Asn Thr His Arg Leu Glu Ser Thr Leu Asn Tyr Gly Phe Glu
            260                 265                 270

Arg Val Trp Thr Ile Cys Cys Leu Lys Gly Ser Asn Val Ala Leu
        275                 280                 285

Gly Tyr Asp Glu Gly Ser Ile Leu Val Lys Val Gly Arg Glu Glu Pro
        290                 295                 300

Ala Val Ser Met Asp Ala Ser Gly Gly Lys Ile Ile Trp Ala Arg His
305                 310                 315                 320

Ser Glu Leu Gln Gln Ala Asn Leu Lys Ala Leu Pro Glu Gly Ala Glu
```

```
                    325                 330                 335
Ile Lys Asp Gly Glu Arg Leu Pro Val Ser Val Lys Asp Met Gly Ala
                340                 345                 350
Cys Glu Ile Tyr Pro Gln Thr Ile Gln His Asn Pro Asn Gly Arg Phe
                355                 360                 365
Val Val Val Cys Gly Asp Gly Glu Tyr Ile Ile Tyr Thr Ala Met Ala
            370                 375                 380
Leu Arg Asn Lys Ala Phe Gly Ser Ala Gln Glu Phe Val Trp Ala Gln
385                 390                 395                 400
Asp Ser Ser Glu Tyr Ala Ile Arg Glu Ser Gly Ser Thr Ile Arg Ile
                405                 410                 415
Phe Lys Asn Phe Lys Glu Lys Asn Phe Lys Ser Asp Phe Gly Ala
                420                 425                 430
Glu Gly Ile Tyr Gly Gly Tyr Leu Leu Gly Val Lys Ser Val Ser Gly
                435                 440                 445
Leu Thr Phe Tyr Asp Trp Asp Thr Leu Asp Leu Val Arg Arg Ile Glu
        450                 455                 460
Ile Gln Pro Lys Ala Val Tyr Trp Ser Asp Ser Gly Lys Leu Val Cys
465                 470                 475                 480
Leu Ala Thr Glu Asp Ser Tyr Phe Ile Leu Ser Tyr Asp Ala Asp Glu
                485                 490                 495
Val Gln Lys Ala Lys Asp Asn Asn Gln Val Ala Asp Asp Gly Val Glu
                500                 505                 510
Ser Ala Phe Asn Leu Leu Gly Glu Ile Asn Glu Ser Val Arg Thr Gly
                515                 520                 525
Leu Trp Val Gly Asp Cys Phe Ile Tyr Thr Asn Ala Val Asn Arg Ile
        530                 535                 540
Asn Tyr Phe Val Gly Gly Glu Leu Val Thr Ile Ala His Leu Asp Arg
545                 550                 555                 560
Pro Leu Tyr Val Leu Gly Tyr Val Pro Lys Asp Asp Arg Leu Tyr Leu
                565                 570                 575
Val Asp Lys Glu Leu Arg Val Val Ser Tyr Gln Leu Leu Leu Ser Val
                580                 585                 590
Leu Glu Tyr Gln Thr Ala Val Met Arg Arg Asp Phe Pro Thr Ala Asp
        595                 600                 605
Arg Val Leu Pro Ser Ile Pro Lys Glu His Arg Thr Arg Val Ala His
        610                 615                 620
Phe Leu Glu Lys Gln Gly Phe Lys Gln Gln Ala Leu Ala Val Ser Ser
625                 630                 635                 640
Asp Pro Glu His Arg Phe Glu Leu Ala Val Ala Leu Glu Asp Leu Asn
                645                 650                 655
Thr Ala Lys Ile Leu Ala Gln Glu Ala Asn Asn Pro Gln Lys Trp Ser
                660                 665                 670
Gln Leu Ala Asp Leu Ala Ala Gly Thr Asn Asn Val Glu Leu Ala Lys
        675                 680                 685
Glu Cys Met Gln Lys Ala Gln Asp Phe Gly Gly Leu Leu Leu Leu Ala
                690                 695                 700
Thr Ser Ser Gly Asp Glu Ser Leu Val Arg Thr Leu Gly Glu Thr Thr
705                 710                 715                 720
Gln Ala Glu Gly Lys His Asn Leu Ala Phe Leu Ser His Phe Leu Val
                725                 730                 735
Gly Asp Leu Asp Lys Cys Leu Asp Ile Leu Val Ser Thr Gly Arg Leu
                740                 745                 750
```

```
Pro Glu Ala Ala Phe Phe Ala Arg Ser Tyr Leu Pro Asp Lys Ile Ser
        755                 760                 765
Glu Val Val Glu Leu Trp Arg Thr Gln Leu Ser Thr Ile Asn Gln Lys
    770                 775                 780
Ala Gly Gln Ser Leu Ala Asp Pro Lys Asn Tyr Glu Asn Leu Phe Pro
785                 790                 795                 800
Gly Leu Gln Gln Ala Leu Ser Ala Gln Lys Phe Leu Glu Gln Asn Lys
                805                 810                 815
Gln Leu Pro Pro Ala Phe Met Ala Pro Ser Ile Val Pro Asn Gln Asp
            820                 825                 830
Arg Asn Val Ile Ala Glu Ala Glu Ala Gln Leu Lys Asn Ser Gly Thr
                835                 840                 845
Ser Ser Asn Leu Phe Ser Ala Pro Pro Ser Ala Glu Thr Ser Arg Asn
        850                 855                 860
Val Ile Glu Ser Val Pro Gln Asn Lys Pro Ser Glu Asp Leu Ser Asn
865                 870                 875                 880
Arg Val Leu Leu Asp Gln Asp Asp Asp Ile Asp Leu Asp Leu
                885                 890                 895
Asp Gly Val Asn Ile Asp Asp Asn Ile Asp Thr Thr Asp Ile Asn Leu
            900                 905                 910
Asp Asp Asp Leu Leu Ser Asp
        915

<210> SEQ ID NO 3
<211> LENGTH: 361
<212> TYPE: DNA
<213> ORGANISM: Monolepta hieroglyphica

<400> SEQUENCE: 3
aggtgtcaat tgtgtagact actaccacgg aggtgataaa ccctatataa tatcaggagc    60
cgatgatagg ttggtcaaaa tctgggatta ccaaaataaa acatgtgttc aaaccttaga   120
aggacatggt caaaatgtta ctgctgtctt tttccatcca gaacttccag ttgctcttac   180
gggaagtgaa gatggtacag tgagaatatg gcatgcaaat acccatcgac tggaaagtac   240
cttaaattat ggatttgaaa gggtttggac catttgttgc ttaaaaggaa gtaataatgt   300
ggcattgggt tatgacgagg gtagtattct tgttaaagtt ggtagagaag aaccagctgt   360
t                                                                  361

<210> SEQ ID NO 4
<211> LENGTH: 423
<212> TYPE: DNA
<213> ORGANISM: Monolepta hieroglyphica

<400> SEQUENCE: 4
gaaaatcaac aactggttaa aacttttgaa gtatgtgaca tacctgttag agctgcaaag    60
tttgtaccta gaaagaactg gattgtcagt ggttcagatg atatgcagat aagagttttt   120
aactacaata cactagacag ggtacactct ttcgaagccc attcagatta tgtgaggtct   180
attgtggtac atccaacaca accatatatt ttaacaagta gtgatgatat gcttatcaaa   240
ctgtggaact gggaaaaggc atgggcttgt cagcaagtgt ttgaaggaca tactcattat   300
attatgcaaa ttgcaataaa tcccaaagac aacaatacat tgccagtgc atctctagat   360 agaacattaa aagtgtggca gctaggtgca tcaacagcta acttcactct tgaagggcat   420
gag                                                                423
```

<210> SEQ ID NO 5
<211> LENGTH: 571
<212> TYPE: DNA
<213> ORGANISM: Monolepta hieroglyphica

<400> SEQUENCE: 5

| | | | | | |
|---|---|---|---|---|---|
| gtctgatttt | ggagctgaag | gtatatatgg | gggttacctt | tgggagtca | aatctgtttc | 60 |
| tgggttaact | ttctatgatt | gggatacact | tgatttggtt | agaaggattg | agatacaacc | 120 |
| aaaagctgtc | tattggtcag | atagtggaaa | gttggtatgt | ttggccaccg | aagatagtta | 180 |
| ttttatttta | tcatatgatg | ctgatgaagt | gcaaaaagct | aaagataata | atcaagttgc | 240 |
| tgacgatggt | gtggaatctg | cattcaacct | tttaggagaa | atcaacgaat | ctgttagaac | 300 |
| aggcctatgg | gtaggtgatt | gtttcatcta | cacaaatgct | gtgaatcgta | tcaattactt | 360 |
| tgtaggaggt | gaactagtaa | ctatcgcaca | cttggatcgt | ccattgtacg | tcttgggtta | 420 |
| tgtgcccaaa | gacgatcgtt | tgtatctagt | agataaagag | ttacgagttg | tcagctacca | 480 |
| attgcttctt | tcagtactcg | aatatcagac | agctgttatg | aggagggact | tcccaacagc | 540 |
| agatagagta | ctaccgtcta | tacctaaaga | g | | | 571 |

<210> SEQ ID NO 6
<211> LENGTH: 780
<212> TYPE: DNA
<213> ORGANISM: Monolepta hieroglyphica

<400> SEQUENCE: 6

| | | | | | |
|---|---|---|---|---|---|
| gcacatttct | tagaaaagca | aggttttaaa | caacaagctt | tagctgtaag | ttccgatccc | 60 |
| gaacatagat | tcgaactcgc | tgtggcatta | gaagacctga | atacagctaa | aattctagca | 120 |
| caagaggcta | acaatccaca | aaagtggagc | caattagctg | atctagctgc | tggcacaaat | 180 |
| aatgtagaac | tagcaaaaga | atgcatgcag | aaagcccaag | attttggtgg | attattactt | 240 |
| ctagccacta | gttcgggaga | tgaatcatta | gtccgtacat | taggtgaaac | aacacaagct | 300 |
| gagggcaaac | ataatttagc | cttcctttct | catttcttgg | taggagattt | agacaagtgt | 360 |
| ctagatattt | tagtaagtac | aggaaggttg | ccagaagctg | cgttttcgc | cagatcttat | 420 |
| cttcccgata | aaatttctga | agttgtagaa | ttgtggagga | cacaattatc | aactataaat | 480 |
| caaaaagccg | acaaagttt | agccgatcct | aaaaattatg | aaaatctatt | tcccggtctt | 540 |
| caacaagcat | tgtcggcaca | gaaattttg | gaacagaaca | aacagttgcc | acctgcattt | 600 |
| atggctcctt | ctattgttcc | caaccaagat | agaaatgtta | tagccgaagc | ggaggcacag | 660 |
| ttaaagaata | gtggaacttc | atcaaatttg | ttcagtgccc | caccttcagc | agaaacttct | 720 |
| aggaatgtta | tagaatcagt | accacaaaat | aagccctcag | aagatttatc | aaacagggtg | 780 |

<210> SEQ ID NO 7
<211> LENGTH: 174
<212> TYPE: DNA
<213> ORGANISM: Monolepta hieroglyphica

<400> SEQUENCE: 7

| | | | | | |
|---|---|---|---|---|---|
| atgccacttc | gattagatat | aaagagaagg | ctaacagccc | gttcagaccg | ggttaaatgc | 60 |
| gtggatcttc | atccgacaga | accctggatg | ttatgttctc | tgtacagtgg | aaatataaat | 120 |
| gtctggaata | ctgaaaatca | acaactggtt | aaaacttttg | aagtatgtga | cata | 174 |

<210> SEQ ID NO 8

<211> LENGTH: 697
<212> TYPE: DNA
<213> ORGANISM: Monolepta hieroglyphica

<400> SEQUENCE: 8

```
tgtacctaga aagaactgga ttgtcagtgg ttcagatgat atgcagataa gagtttttaa      60
ctacaataca ctagacaggg tacactcttt cgaagcccat tcagattatg tgaggtctat     120
tgtggtacat ccaacacaac catatatttt aacaagtagt gatgatatgc ttatcaaact     180
gtggaactgg gaaaaggcat gggcttgtca gcaagtgttt gaaggacata ctcattatat     240
tatgcaaatt gcaataaatc ccaaagacaa caatacattt gccagtgcat ctctagatag     300
aacattaaaa gtgtggcagc taggtgcatc aacagctaac ttcactcttg aagggcatga     360
gaaaggtgtc aattgtgtag actactacca cggaggtgat aaaccctata taatatcagg     420
agccgatgat aggttggtca aaatctggga ttaccaaaat aaaacatgtg ttcaaacctt     480
agaaggacat ggtcaaaatg ttactgctgt cttttttccat ccagaacttc cagttgctct     540
tacgggaagt gaagatggta cagtgagaat atggcatgca ataccccatc gactggaaag     600
taccttaaat tatggatttg aaagggtttg gaccatttgt tgcttaaaag gaagtaataa     660
tgtggcattg ggttatgacg agggtagtat tcttgtt                              697
```

<210> SEQ ID NO 9
<211> LENGTH: 342
<212> TYPE: DNA
<213> ORGANISM: Monolepta hieroglyphica

<400> SEQUENCE: 9

```
ctgttagtat ggatgccagt ggtggtaaaa ttatttgggc taggcactca gaactccaac      60
aagccaatct taaggcattg cctgaaggtg ctgaaataaa agatggagaa cgacttccag     120
tatctgtaaa ggatatgggt gcctgtgaaa tctatcctca aaccattcaa cacaatccca     180
atggtcgttt tgtagttgtg tgtggagatg gtgaatatat aatttacact gccatggcct     240
tacgtaacaa agcatttgga agtgcacaag aattcgtttg ggcccaagat tctagtgaat     300
atgctattag agaatcagga tctactataa ggatatttaa aa                        342
```

<210> SEQ ID NO 10
<211> LENGTH: 139
<212> TYPE: DNA
<213> ORGANISM: Monolepta hieroglyphica

<400> SEQUENCE: 10

```
aagtctgatt ttggagctga aggtatatat ggggggttacc ttttgggagt caaatctgtt      60
tctgggttaa cttttctatga ttgggataca cttgatttgg ttagaaggat tgagatacaa     120
ccaaaagctg tctattggt                                                   139
```

<210> SEQ ID NO 11
<211> LENGTH: 821
<212> TYPE: DNA
<213> ORGANISM: Monolepta hieroglyphica

<400> SEQUENCE: 11

```
catatgatgc tgatgaagtg caaaaagcta agataataa tcaagttgct gacgatggtg       60
tggaatctgc attcaacctt ttaggagaaa tcaacgaatc tgttagaaca ggcctatggg     120
taggtgattt tttcatctac acaaatgctg tgaatcgtat caattacttt gtaggaggtg     180
aactagtaac tatcgcacac ttggatcgtc cattgtacgt cttgggttat gtgcccaaag     240
```

```
acgatcgttt gtatctagta gataaagagt tacgagttgt cagctaccaa ttgcttcttt     300
cagtactcga atatcagaca gctgttatga ggagggactt cccaacagca gatagagtac     360
taccgtctat acctaaagag cacagaacaa gggtagcaca tttcttagaa aagcaaggtt     420
ttaaacaaca agctttagct gtaagttccg atcccgaaca tagattcgaa ctcgctgtgg     480
cattagaaga cctgaataca gctaaaattc tagcacaaga ggctaacaat ccacaaaagt     540
ggagccaatt agctgatcta gctgctggca caaataatgt agaactagca aaagaatgca     600
tgcagaaagc ccaagatttt ggtggattat tacttctagc cactagttcg ggagatgaat     660
cattagtccg tacattaggt gaaacaacac aagctgaggg caaacataat ttagccttcc     720
tttctcattt cttggtagga gatttagaca agtgtctaga tattttagta agtacaggaa     780
ggttgccaga agctgcgttt ttcgccagat cttatcttcc c                         821
```

<210> SEQ ID NO 12
<211> LENGTH: 316
<212> TYPE: DNA
<213> ORGANISM: Monolepta hieroglyphica

<400> SEQUENCE: 12

```
gaattgtgga ggacacaatt atcaactata aatcaaaaag ccggacaaag tttagccgat      60
cctaaaaatt atgaaaatct atttcccggt cttcaacaag cattgtcggc acagaaattt     120
ttggaacaga acaaacagtt gccacctgca tttatggctc cttctattgt tcccaaccaa     180
gatagaaatg ttatagccga agcggaggca cagttaaaga atagtggaac ttcatcaaat     240
ttgttcagtg ccccaccttc agcagaaact tctaggaatg ttatagaatc agtaccacaa     300
aataagccct cagaag                                                     316
```

<210> SEQ ID NO 13
<211> LENGTH: 174
<212> TYPE: DNA
<213> ORGANISM: Monolepta hieroglyphica

<400> SEQUENCE: 13

```
atgccacttc gattagatat aaagagaagg ctaacagccc gttcagaccg ggttaaatgc      60
gtggatcttc atccgacaga accctggatg ttatgttctc tgtacagtgg aaatataaat     120
gtctggaata ctgaaaatca acaactggtt aaaacttttg aagtatgtga cata            174
```

<210> SEQ ID NO 14
<211> LENGTH: 361
<212> TYPE: DNA
<213> ORGANISM: Monolepta hieroglyphica

<400> SEQUENCE: 14

```
tgtacctaga aagaactgga ttgtcagtgg ttcagatgat atgcagataa gagttttttaa     60 ctacaataca ctagacaggg tacactcttt cgaagcccat tcagattatg tgaggtctat     120
tgtggtacat ccaacacaac catatatttt aacaagtagt gatgatatgc ttatcaaact     180
gtggaactgg gaaaaggcat gggcttgtca gcaagtgttt gaaggacata ctcattatat     240
tatgcaaatt gcaataaatc ccaaagacaa caatacattt gccagtgcat ctctagatag     300
aacattaaaa gtgtggcagc taggtgcatc aacagctaac ttcactcttg aagggcatga     360
g                                                                     361
```

<210> SEQ ID NO 15

```
<211> LENGTH: 334
<212> TYPE: DNA
<213> ORGANISM: Monolepta hieroglyphica

<400> SEQUENCE: 15
aggtgtcaat tgtgtagact actaccacgg aggtgataaa ccctatataa tatcaggagc      60
cgatgatagg ttggtcaaaa tctgggatta ccaaaataaa acatgtgttc aaaccttaga    120
aggacatggt caaaatgtta ctgctgtctt tttccatcca gaacttccag ttgctcttac    180
gggaagtgaa gatggtacag tgagaatatg gcatgcaaat acccatcgac tggaaagtac    240
cttaaattat ggatttgaaa gggtttggac catttgttgc ttaaaaggaa gtaataatgt    300
ggcattgggt tatgacgagg gtagtattct tgtt                                 334

<210> SEQ ID NO 16
<211> LENGTH: 342
<212> TYPE: DNA
<213> ORGANISM: Monolepta hieroglyphica

<400> SEQUENCE: 16
ctgttagtat ggatgccagt ggtggtaaaa ttatttgggc taggcactca gaactccaac      60
aagccaatct taaggcattg cctgaaggtg ctgaaataaa agatggagaa cgacttccag    120
tatctgtaaa ggatatgggt gcctgtgaaa tctatcctca aaccattcaa cacaatccca    180
atggtcgttt tgtagttgtg tgtggagatg gtgaatatat aatttacact gccatggcct    240
tacgtaacaa agcatttgga agtgcacaag aattcgtttg ggcccaagat tctagtgaat    300
atgctattag agaatcagga tctactataa ggatatttaa aa                        342

<210> SEQ ID NO 17
<211> LENGTH: 139
<212> TYPE: DNA
<213> ORGANISM: Monolepta hieroglyphica

<400> SEQUENCE: 17
aagtctgatt ttggagctga aggtatatat ggggggttacc ttttgggagt caaatctgtt     60
tctgggttaa ctttctatga ttgggataca cttgatttgg ttagaaggat tgagatacaa    120
ccaaaagctg tctattggt                                                  139

<210> SEQ ID NO 18
<211> LENGTH: 380
<212> TYPE: DNA
<213> ORGANISM: Monolepta hieroglyphica

<400> SEQUENCE: 18
catatgatgc tgatgaagtg caaaaagcta agataataaa tcaagttgct gacgatggtg      60
tggaatctgc attcaacctt ttaggagaaa tcaacgaatc tgttagaaca ggcctatggg    120
taggtgattt tttcatctac acaaatgctg tgaatcgtat caattacttt gtaggaggtg    180
aactagtaac tatcgcacac ttggatcgtc cattgtacgt cttgggttat gtgcccaaag    240
acgatcgttt gtatctagta gataaagagt tacgagttgt cagctaccaa ttgcttctttt    300
cagtactcga atatcagaca gctgttatga ggagggactt cccaacagca gatagagtac    360
taccgtctat acctaaagag                                                380

<210> SEQ ID NO 19
<211> LENGTH: 426
<212> TYPE: DNA
<213> ORGANISM: Monolepta hieroglyphica
```

<400> SEQUENCE: 19

```
gcacatttct tagaaaagca aggttttaaa caacaagctt tagctgtaag ttccgatccc    60
gaacatagat tcgaactcgc tgtggcatta aagacctga atacagctaa aattctagca   120
caagaggcta acaatccaca aaagtggagc caattagctg atctagctgc tggcacaaat   180
aatgtagaac tagcaaaaga atgcatgcag aaagcccaag attttggtgg attattactt   240
ctagccacta gttcgggaga tgaatcatta gtccgtacat taggtgaaac aacacaagct   300
gagggcaaac ataatttagc cttccttcct catttcttgg taggagattt agacaagtgt   360
ctagatattt tagtaagtac aggaaggttg ccagaagctg cgttttttcgc cagatcttat   420 cttccc                                                              426
```

<210> SEQ ID NO 20
<211> LENGTH: 316
<212> TYPE: DNA
<213> ORGANISM: Monolepta hieroglyphica

<400> SEQUENCE: 20

```
gaattgtgga ggacacaatt atcaactata aatcaaaaag ccggacaaag tttagccgat    60
cctaaaaatt atgaaaatct atttcccggt cttcaacaag cattgtcggc acagaaattt   120
ttggaacaga acaaacagtt gccacctgca tttatggctc cttctattgt tcccaaccaa   180
gatagaaatg ttatagccga agcggaggca cagttaaaga atagtggaac ttcatcaaat   240
ttgttcagtg ccccaccttc agcagaaact tctaggaatg ttatagaatc agtaccacaa   300
aataagccct cagaag                                                   316
```

<210> SEQ ID NO 21
<211> LENGTH: 328
<212> TYPE: DNA
<213> ORGANISM: Cauliflower mosaic virus

<400> SEQUENCE: 21

```
ccattgccca gctatctgtc actttattgt gaagatagtg aaaaggaag gtggctccta    60 caaatgccat cattgcgata aaggaaaggc catcgttgaa gatgcctctg ccgacagtgg   120
tcccaaagat ggacccccac ccacgaggag catcgtggaa aaagaagacg ttccaaccac   180
gtcttcaaag caagtggatt gatgtgatat ctccactgac gtaagggatg acgcacaatc   240
ccactatcct tcgcaagacc cttcctctat ataaggaagt tcatttcatt tggagaggac   300
acgctgacaa gctgactcta gcagatct                                      328
```

<210> SEQ ID NO 22
<211> LENGTH: 872
<212> TYPE: DNA
<213> ORGANISM: Artificial Sequence
<220> FEATURE:
<223> OTHER INFORMATION: R1 nucleotide sequence

<400> SEQUENCE: 22

```
aggtgtcaat tgtgtagact actaccacgg aggtgataaa ccctatataa tatcaggagc    60
cgatgatagg ttggtcaaaa tctgggatta ccaaaataaa acatgtgttc aaaccttaga   120
aggacatggt caaaatgtta ctgctgtctt tttccatcca gaacttccag ttgctcttac   180
gggaagtgaa gatggtacag tgagaatatg gcatgcaaat acccatcgac tggaaagtac   240
cttaaattat ggatttgaaa gggtttggac catttgttgc ttaaaaggaa gtaataatgt   300
```

| | |
|---|---:|
| ggcattgggt tatgacgagg gtagtattct tgttaaagtt ggtagagaag aaccagctgt | 360 |
| taagtactgc gatcgcgtta acgctttatc acgatacctt ctaccacata tcactaacaa | 420 |
| catcaacact catcactctc gacgacatcc actcgatcac tactctcaca cgaccgatta | 480 |
| actcctcatc cacgcggccg cctgcaggag caacagctgg ttcttctcta ccaactttaa | 540 |
| caagaatact accctcgtca tacccaatg ccacattatt acttcctttt aagcaacaaa | 600 |
| tggtccaaac cctttcaaat ccataattta aggtactttc cagtcgatgg gtatttgcat | 660 |
| gccatattct cactgtacca tcttcacttc ccgtaagagc aactggaagt tctggatgga | 720 |
| aaaagacagc agtaacattt tgaccatgtc cttctaaggt ttgaacacat gтттттатттт | 780 |
| ggtaatccca gатттттgacc aacctatcat cggctcctga tattatatag ggtttatcac | 840 |
| ctccgtggta gtagtctaca caattgacac ct | 872 |

<210> SEQ ID NO 23
<211> LENGTH: 150
<212> TYPE: DNA
<213> ORGANISM: Artificial Sequence
<220> FEATURE:
<223> OTHER INFORMATION: Spacer sequence

<400> SEQUENCE: 23

| | |
|---|---:|
| aagtactgcg atcgcgttaa cgcttt atca cgataccttc taccacatat cactaacaac | 60 |
| atcaacactc atcactctcg acgacatcca ctcgatcact actctcacac gaccgattaa | 120 |
| ctcctcatcc acgcggccgc ctgcaggagc | 150 |

<210> SEQ ID NO 24
<211> LENGTH: 253
<212> TYPE: DNA
<213> ORGANISM: Agrobacterium tumefaciens

<400> SEQUENCE: 24

| | |
|---|---:|
| gatcgttcaa acatttggca ataaagtttc ttaagattga atcctgttgc cggtcttgcg | 60 |
| atgattatca tataatttct gttgaattac gttaagcatg taataattaa catgtaatgc | 120 |
| atgacgttat ttatgagatg gtttttatg attagagtcc cgcaattata catttaatac | 180 |
| gcgatagaaa acaaaatata gcgcgcaaac taggataaat tatcgcgcgc ggtgtcatct | 240 |
| atgttactag atc | 253 |

<210> SEQ ID NO 25
<211> LENGTH: 1026
<212> TYPE: DNA
<213> ORGANISM: Salmonella enterica

<400> SEQUENCE: 25

| | |
|---|---:|
| atgaaaaagc ctgaactcac cgcgacgtct gtcgagaagt ttctgatcga aagttcgac | 60 |
| agcgtctccg acctgatgca gctctcggag ggcgaagaat ctcgtgcttt cagcttcgat | 120 |
| gtaggagggc gtggatatgt cctgcgggta aatagctgcg ccgatggttt ctacaaagat | 180 |
| cgttatgttt atcggcactt tgcatcggcc gcgctcccga ttccggaagt gcttgacatt | 240 |
| ggggaattca gcgagagcct gacctattgc atctcccgcc gtgcacaggg tgtcacgttg | 300 |
| caagacctgc ctgaaaccga actgcccgct gttctgcagc cggtcgcgga ggccatggat | 360 |
| gcgatcgctg cggccgatct tagccagacg agcgggttcg gcccattcgg accgcaagga | 420 |
| atcggtcaat acactacatg gcgtgatttc atatgcgcga ttgctgatcc ccatgtgtat | 480 |
| cactggcaaa ctgtgatgga cgacaccgtc agtgcgtccg tcgcgcaggc tctcgatgag | 540 |

```
ctgatgcttt gggccgagga ctgccccgaa gtccggcacc tcgtgcacgc ggatttcggc    600
tccaacaatg tcctgacgga caatggccgc ataacagcgg tcattgactg agcgaggcg    660 atgttcgggg attcccaata cgaggtcgcc aacatcttct tctggaggcc gtggttggct    720
tgtatggagc agcagacgcg ctacttcgag cggaggcatc cggagcttgc aggatcgccg    780
cggctccggg cgtatatgct ccgcattggt cttgaccaac tctatcagag cttggttgac    840
ggcaatttcg atgatgcagc ttgggcgcag ggtcgatgcg acgcaatcgt ccgatccgga    900
gccgggactg tcgggcgtac acaaatcgcc cgcagaagcg cggccgtctg gaccgatggc    960
tgtgtagaag tactcgccga tagtggaaac cgacgcccca gcactcgtcc gagggcaaag   1020
gaatag                                                              1026

<210> SEQ ID NO 26
<211> LENGTH: 20
<212> TYPE: DNA
<213> ORGANISM: Artificial Sequence
<220> FEATURE:
<223> OTHER INFORMATION: Primer 1

<400> SEQUENCE: 26
cagggtgtca cgttgcaaga                                                20

<210> SEQ ID NO 27
<211> LENGTH: 20
<212> TYPE: DNA
<213> ORGANISM: Artificial Sequence
<220> FEATURE:
<223> OTHER INFORMATION: Primer 2

<400> SEQUENCE: 27
ccgctcgtct ggctaagatc                                                20

<210> SEQ ID NO 28
<211> LENGTH: 24
<212> TYPE: DNA
<213> ORGANISM: Artificial Sequence
<220> FEATURE:
<223> OTHER INFORMATION: Probe 1

<400> SEQUENCE: 28
tgcctgaaac cgaactgccc gctg                                           24

<210> SEQ ID NO 29
<211> LENGTH: 334
<212> TYPE: DNA
<213> ORGANISM: Artificial Sequence
<220> FEATURE:
<223> OTHER INFORMATION: irrelevant dsRNA

<400> SEQUENCE: 29
ggaaatcgcc actgctaaga aaaatggaca gaaaaataag agagcggcac ttcaagcact     60
caagcggaag aagcggtatg agaaacagtt gcagcagatt gatggaacat tatcaactat    120
tgaaatgcag agagaagctt tagagggtgc caacactaat acagctgttc tcacaacaat    180
gaaagatgct gcggacgccc tcaaagctgc tcacaaacac atggatgtcg atcaagttca    240
tgatatgatg gatgacattg ccgaacagca agatgtagct agagaaattt ctgatgccat    300
atccaaccca gttgcatttg gtcatgatat tgat                                334

<210> SEQ ID NO 30
```

```
<211> LENGTH: 541
<212> TYPE: DNA
<213> ORGANISM: Monolepta hieroglyphica

<400> SEQUENCE: 30
atttgttgat actagtggta gacataaaca agaagaatca ctatttgaag aaatgttggc      60
agtttctaat gctgtgagac cagataatat tattttcgtt atggatgcaa ctattggtca     120
agcttgtgag tctcaggcta aagctttcaa agaaaaggta gatgtaggct ctgtaattat     180
aacaaaatta gatggacatg caaaaggagg tggtgcactc agtgctgtgg cagccactaa     240
cagtcctatt atattcattg gtacaggaga acatatagat gacttagaac cttttaaaac     300
aaaacctttc attagtaaat tattaggaat gggtgatata gaaggtttaa ttgataaagt     360
aaacgaatta aagttagagg ataatgaaga attgttagaa aaaattaaac atgggcaatt     420
cacactcaga gacatgtatg aacagttcca aaatattatg aaaatgggac ctttctcaca     480
aataatggga atgatccctg gatttagcca agatttcatg tcaaaaggaa gtgaacaaga     540
a                                                                     541

<210> SEQ ID NO 31
<211> LENGTH: 394
<212> TYPE: DNA
<213> ORGANISM: Monolepta hieroglyphica

<400> SEQUENCE: 31
aataatggac agtatgaatg attatgaatt agataaccga gatggtgcaa aattatttac      60
aaagcaaaat ggtagagtta ttagagttgc acaagggtct ggtgttacag aaagagaagt     120
aaaagatttg atcacgcaat acacgaagtt tgccgccgta gtaaagaaaa tgggcggcat     180
aaagggtctt tttaaaggcg gcgatatggc taaaaatgtc aatcacaacc aaatggccaa     240
acttaatcaa caaatggcca agatgatgga tcctcgagtg cttcagcaaa tgggcggcat     300
ggctggatta cagaacatga tgagacagct acaagcgggc gcggcaggag gcttgggagg     360
tttgggtaac cttatgggtg gttttggagg gaaa                                 394
```